(12) United States Patent
Sugiyama et al.

(10) Patent No.: US 8,058,038 B2
(45) Date of Patent: Nov. 15, 2011

(54) ALDOLASE AND PRODUCTION PROCESS OF SUBSTITUTED α-KETO ACIDS

(75) Inventors: Masakazu Sugiyama, Kanagawa (JP); Kunihiko Watanabe, Kanagawa (JP); Shigeru Kawahara, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 517 days.

(21) Appl. No.: 11/960,116

(22) Filed: Dec. 19, 2007

(65) Prior Publication Data

US 2008/0318290 A1 Dec. 25, 2008

Related U.S. Application Data

(60) Division of application No. 11/066,542, filed on Feb. 28, 2005, now Pat. No. 7,351,569, which is a continuation of application No. PCT/JP03/10750, filed on Aug. 26, 2003.

(30) Foreign Application Priority Data

Aug. 26, 2002 (JP) ................. 2002-245980
Jun. 16, 2003 (JP) ................. 2003-171299

(51) Int. Cl.
C12P 7/44 (2006.01)
C12P 7/40 (2006.01)
C12P 7/50 (2006.01)
C12P 17/10 (2006.01)
C12P 7/42 (2006.01)
C07K 14/00 (2006.01)
C12N 9/10 (2006.01)
C12N 9/88 (2006.01)

(52) U.S. Cl. ........ 435/136; 435/142; 435/143; 435/121; 435/146; 435/193; 435/232; 530/350

(58) Field of Classification Search ............. 435/142, 435/143, 69.1, 121, 146, 193, 232; 530/350
See application file for complete search history.

(56) References Cited

U.S. PATENT DOCUMENTS

| | | |
|---|---|---|
| 3,751,458 A | 8/1973 | Wiley |
| 4,975,298 A | 12/1990 | Van Wyk et al. |
| 5,128,482 A | 7/1992 | Olivier et al. |
| 5,994,559 A | 11/1999 | Abushanab et al. |
| 7,064,219 B2 | 6/2006 | Kawahara et al. |
| 7,241,599 B2 | 7/2007 | Sugiyama et al. |
| 7,244,462 B2 | 7/2007 | Amino et al. |
| 7,297,800 B2 | 11/2007 | Sugiyama et al. |
| 7,329,427 B2 | 2/2008 | Amino et al. |
| 7,351,569 B2 | 4/2008 | Sugiyama et al. |
| 7,371,549 B2 | 5/2008 | Sugiyama et al. |
| 7,390,909 B2 | 6/2008 | Kawahara et al. |
| 7,396,941 B2 | 7/2008 | Mori et al. |
| 7,402,412 B2 | 7/2008 | Sugiyama et al. |
| 7,432,100 B2 | 10/2008 | Sugiyama et al. |
| 7,534,590 B2 | 5/2009 | Mori et al. |
| 7,534,898 B2 | 5/2009 | Amino et al. |
| 7,553,974 B2 | 6/2009 | Mori et al. |
| 7,572,607 B2 | 8/2009 | Hicks et al. |
| 7,612,214 B2 | 11/2009 | Amino et al. |
| 7,662,596 B2 | 2/2010 | Sugiyama et al. |
| 7,678,925 B2 | 3/2010 | Kawahara et al. |
| 7,781,005 B2 | 8/2010 | Mori |
| 2005/0009153 A1 | 1/2005 | Sugiyama et al. |
| 2005/0020508 A1 | 1/2005 | Amino et al. |
| 2005/0244937 A1 | 11/2005 | Abraham et al. |
| 2005/0272939 A1 | 12/2005 | Amino et al. |
| 2005/0282260 A1 | 12/2005 | Hicks et al. |
| 2006/0083695 A1 | 4/2006 | Mori |
| 2007/0072277 A1 | 3/2007 | Sugiyama et al. |
| 2008/0091032 A1 | 4/2008 | Kawahara et al. |
| 2008/0193975 A1 | 8/2008 | Sugiyama et al. |
| 2008/0193984 A1 | 8/2008 | Sugiyama et al. |
| 2008/0199921 A1 | 8/2008 | Sugiyama et al. |
| 2008/0207920 A1 | 8/2008 | Kawahara et al. |
| 2009/0259052 A1 | 10/2009 | Kawahara et al. |
| 2009/0318528 A1 | 12/2009 | Mori et al. |
| 2010/0184165 A1 | 7/2010 | Sugiyama et al. |

FOREIGN PATENT DOCUMENTS

| | | |
|---|---|---|
| CN | 1656068 | 8/2005 |
| EP | 0 438 314 | 7/1991 |
| EP | 1 045 029 A2 | 10/2000 |
| EP | 1 045 029 A3 | 10/2000 |
| JP | 64-025757 | 1/1989 |
| JP | 04-217654 | 8/1992 |
| JP | 2002-60382 | 2/2002 |
| WO | 03/056026 A1 | 7/2003 |
| WO | WO 03/059865 | 7/2003 |
| WO | 03/091396 | 11/2003 |

OTHER PUBLICATIONS

U.S. Appl. No. 12/613,713, filed Nov. 6, 2009, Kawahara, et al.
U.S. Appl. No. 12/613,839, filed Nov. 6, 2009, Sugiyama, et al.
105,696, Jun. 25, 2009, Kawahara, et al.
K. Maruyama, et al., "Cloning, Sequencing, and Expression of the Gene Encoding 4-Hydroxy-4-Methyl-2-Oxoglutarate Aldolase From *Pseudomonas ochraceae* NGJ1", Biosei. Biotechnol. Biochem., 65 (12), pp. 2701-2709, 2001.
"Probable Transferase Protein (EC2.-.-.-)," retrieved from EBI accession No. UNIPROT: Q8XRB4, (Mar. 1, 2002).
"*Acinetobacter baumannii* protein #3236," retrieved from EBI accession No. GSP:ADA36075, (Nov. 20, 2003).
Demethylmenaquinone methyltransferase (AGR_pAT_472p), retrieved from EBI accession No. UNIPROT: Q8UJZ5, (Jun. 1, 2002).
Tack, B. F., et al., "Purification and Properties of 4-Hydroxy-4-methyl-2-oxoglutarate Aldolase," Journal of Biological Chemistry, vol. 247, No. 20, 1972, pp. 6444-6449.

(Continued)

Primary Examiner — Delia Ramirez
(74) Attorney, Agent, or Firm — Oblon, Spivak, McClelland, Maier & Neustadt, L.L.P.

(57) ABSTRACT

4-(Indol-3-ylmethyl)-4-hydroxy-2-oxoglutarate, which is useful as an intermediate in the synthesis of monatin, may be synthesized from indole pyruvic acid and pyruvic acid (and/or oxalacetic acid) by using a novel aldolase derived from the genus *Pseudomonas, Erwinia, Flavobacterium,* or *Xanthomonas*.

19 Claims, 4 Drawing Sheets

OTHER PUBLICATIONS

Maruyama, K., "Purification and Properties of 4-Hydroxy-4-Methyl-2-Oxoglutarate Aldolase from *Pseudomonas ochraceae* Grown on Phthalate," Journal of Biochemistry, vol. 108, No. 2, 1990, pp. 327-333.

Patil, R. V., et al., "Cloning, Nucleotide Sequence, Overexpression, and Inactivation of the *Excherichia coli* 2-Keto-4-Hydroxyglutarate Aldolase Gene," Journal of Bacteriology, vol. 174, No. 1, Jan. 1992, pp. 102-107.

Liu, J. Q, et al., "Gene Cloning, Biochemical Characterization and Physiological Role of a Thermostable Low-Specificity L-Threonine Aldolase from *Escherichia coli*," European Journal of Biochemistry, vol. 255, No. 1, Jul. 1998, pp. 220-226.

Liu, J. Q., et al., "Low-Specificity L-Threonine Aldolase of *Pseudomonas* sp. NCIMB 10558: Purification, Characterization and its Application of β-hydroxy-α-amino Acid Synthesis," Applied Microbiology and Biotechnology, vol. 49, No. 6, Jun. 1998, pp. 702-708.

Leung, P. T., et al., "Purification and Properties of 4-Hydroxy-2-Ketopimelate Aldolase from *Acinetobacter*," Journal of Bacteriology, vol. 120, No. 1, 1974, pp. 168-172.

Fessner, W. D., et al., "Biocatalytic Synthesis of Hydroxylated Natural Products Using Aldolases and Related Enzymes," Current Opinion in Biotechnology, vol. 12, No. 6, Dec. 2001, pp. 574-586.

U.S. Appl. No. 12/768,360, filed Apr. 27, 2010, Sugiyama, et al.
U.S. Appl. No. 12/758,433, filed Apr. 12, 2010, Sugiyama, et al.
U.S. Appl. No. 12/825,886, filed Jun. 29, 2010, Amino, et al.
U.S. Appl. No. 12/853,844, filed Aug. 10, 2010, Sugiyama et al.
U.S. Appl. No. 07/178,323, filed Apr. 6, 1988, Amino, et al.

K. Juhl, et al., "Catalytic Asymmetric Homo-Aldol Reaction of Pyruvate-A Chiral Lewis Acid Catalyst That Mimies Aldolase Enzymes", Chemical Communications, 2000, No. 22, pp. 2211-2212.

G. Buldain, et al., "Carbon-13 Nuclear Magnetic Resonance Spectra of the Hydrate, ETO and ENOL Forms of Oxalacetic Acid", Magnetic Resonance in Chemistry, 1985, vol. 23, No. 6, pp. 478-481.

D. Oliveira, et al., "Diastereoselective Formation of a Quaternary Center in a Pyroglutamate Derivative. Formal Synthesis of Monatain", Tetrahedron Letters, vol. 42, 2001, pp. 6793-6796.

K. Nakamura, et al., "Total Synthesis of Monatin", Organic Letters, vol. 2, No. 19, 2000, pp. 2967-2970.

C. Holzapfel, "A Simple Cycloaddition Approach to a Racemate of the Natural Sweetener Monatin", Synthetic Communications, vol. 24, No. 22, 1994, pp. 3197-3211.

C. Holzapfel, "The Synthesis of a -Keto—Amino Acid, A Key Intermediate in the Synthesis of Monatin, A New Natural Sweetener", Synthetic Communications, vol. 23, No. 18, 1993, pp. 2511-2526.

T. Kitahara, et al., Japanese Agrochemical Association, the 2000th Conference, Abstracts of Proceeding, 3B128β, p. 221.

R. Wiley, et al., "The Bimolecular Decarboxylative Self-Condensation of Oxaloacetic Acid to Citroylformic Acid and Its Conversion by Oxidative Decarboxylation to Citric Acid", J. Org. Chem., vol. 38, No. 20, 1973, pp. 3582-3585.

D. Lessing, et al., "A Nuclear Magnetic Resonance Study of Aqueous Pyruvate-Glycinate-Zinc(II) and Related Systems", Journal of American Chemical Society, vol. 86, Jul. 20, 1964, pp. 2805-2810.

S. Margolis, et al., "Identification and Quantitatior of the Impurities in Sodium Pyruvate", Analytical Chemistry, vol. 58, No. 12, 1986, pp. 2504-2510.

N. Passerate, et al., "Large Scale Enzymatic Synthesis of Diastereoisomeric -Hydroxy L-Glutamic Acids", Tetrahedron Letters, vol. 28, No. 12, 1987, pp. 1277-1280.

Kozo Nakamura et al., "Total Synthesis of Monatin", Organic Letters, vol. 2, No. 19, p. 2967-2970 (2000).

Cedric W. Holzapfel., "A Simple Cycloaddition Approach to a Racemate of the Natural Sweetener Monatin", Synthetic Communications, vol. 24, No. 22, p. 3197-3211 (1994).

Abraham et al., 2003, CAS: 139:36397.

Interference No. 105,696: Kawahara's Reply No. 1 (in support of Kawahara's Request to Designate Claim 5 As Corresponding to the Count) and the exhibits cited therein.

Interference No. 105,696: Abraham Opposition 1 (Opposing Kawahara's Request to Designate Claim 5 As Corresponding to the Count) and the exhibits cited therein.

Interference No. 105,696: Kawahara's Preliminary Motion No. 1 (37 C.F.R. 41.208(a)(2) Motion to Designate Claim 5 of Patent 7,064,219 B2 as Corresponding to the Count and the exhibits cited therein.

Interference No. 105,696: Kawahara Preliminary Motion 2 (37 C.F.R. §41.121(a)(1)(ii) and §41.208(a)(3) Motion for Benefit of JP 2001-396300 filed Dec. 27, 2001; JP2002-149069, filed May 23, 2002, JP 2002-149078, filed May 23, 2002; JP-2002-182032, filed Jun. 21, 2002, and PCT/JP02/12473) and the exhibits cited therein.

Interference No. 105,696: Abraham Opposition 2 (Opposing Kawahara's Request for Benefit to Four Earlier Applications) and the exhibits cited therein.

Interference No. 105,696: Kawahara Reply No. 2 (Motion for Benefit of JP 2001-396300 Filed Dec. 27, 2001; JP2002-149069, filed May 23, 2002; JP 2002-149078, filed May 23, 2002; JP-2002-182032, filed Jun. 21, 2002, and PCT/JP02/12473) and the exhibits cited therein.

Interference No. 105,696: Kawahara's Preliminary Motion 3 (Pursuant to 37 C.F.R. § 41.121(a)(2) and 37 C.F.R. §1.324 to Correct the Inventorship of United States Patent No. 7,064,219) and the exhibits cited therein.

Interference No. 105,696: Abraham Opposition 3 (Opposing Kawahara's Request to Correct Inventorship for U.S. Patent No. 7,064,219) and the exhibits cited therein.

Interference No. 105,696 Kawahara Reply No. 3. and the exhibits cited therein.

Interference No. 105,696 Kawahara Preliminary Motion 4 (37 C.F.R. § 41.121(a)(1)(ii) Motion to Deny Abraham Benefit of U.S. Appl. No. 60/374,831 for Lack of Enablement and Written Description) and the exhibits cited therein.

Interference No. 105,696 Abraham Opposition 4 (Opposing Kawahara's Attack on Abraham's Accorded Benefit) and the exhibits cited therein.

Interference No. 105,696 Kawahara's Reply No. 4 (in Support of Kawahara's Motion to Deny Abraham Benefit of U.S. Appl. No. 60/374,831 for Lack of Enablement and Written Description) and the exhibits cited therein.

Interference No. 105,696 Abraham Motion 1 (Seeking Judgment That Kawahara's Involved Claims Lack Written Description) and the exhibits cited therein.

Interference No. 105,696 Kawahara's Opposition to Abraham Motion 1 and the exhibits cited therein.

Interference No. 105,696 Abraham Reply 1 (Seeking Judgment That Kawahara's Involved Claims Lack Written Description) and the exhibits cited therein.

Interference No. 105,696 Abraham Motion 2 (Seeking Judgment That Kawahara's Involved Claims Are Not Enabled) and the exhibits cited therein.

Interference No. 105,696 Kawahara Opposition No. 2 (opposing judgment that Kawahara's involved claims are not enabled) and the exhibits cited therein.

Interference No. 105,696 Abraham Reply 2 (Seeking Judgment That Kawahara's Involved Claims Are Not Enabled) and the exhibits cited therein.

Interference No. 105,696 Abraham Motion 3 (to Substitute Count 1 with Proposed Count 2) and the exhibits cited therein.

Interference No. 105,696 Kawahara's Opposition No. 3 (Corrected) (Opposing Abraham's Motion 3 to Substitute Count 1 with Proposed Count 2) and the exhibits cited therein.

Interference No. 105.696 Abraham Reply 3 (to Substitute Count 1 with Proposed Count 2) and the exhibits cited therein.

Branden et al., Introduction to Protein Structure, Garland Publishing Inc, New York pp. 247, 1991.

Witkowski et al., Biochemistry 38:11643-11650,1999.

Seffernick et al., J. Bacteriol. 183(8):2405-2410,2001.

European Search Repport issued Dec. 2, 2010, in Application No. 10177313.3-2405.

Kozo Nakamura, et al., "Total Synthesis of Monatin", Organic Letters, vol. 2, No. 9, 2000, pp. 2967-2970.

U.S. Appl. No. 13/081,024, filed Apr. 6, 2011, Amino, et al.
U.S. Appl. No. 13/044,618, filed Mar. 10, 2011, Sugiyama, et al.

ALDOLASE AND PRODUCTION PROCESS OF SUBSTITUTED α-KETO ACIDS

CROSS-REFERENCE TO RELATED APPLICATIONS

The present application is a divisional of U.S. Ser. No. 11/066,542 (now U.S. Pat. No. 7,351,569), filed on Feb. 28, 2005, which is a continuation of PCT/JP03/10750, filed on Aug. 26, 2003, and claims priority to JP 2002-245980, filed on Aug. 26, 2002, and JP 2003-171299, filed on June 16, 2003.

BACKGROUND OF THE INVENTION

1. Field of the Invention

The present invention relates to an aldolase and a process for producing substituted α-keto acid, and more particularly, to an aldolase that may be preferably used in the synthesis of 4-(indol-3-ylmethyl)-4-hydroxy-2-oxoglutarate (hereinafter, "IHOG"), which is useful as an intermediate in monatin synthesis, and a process for producing substituted α-keto acids.

2. Discussion of the Background

Monatin, which has the structure shown in formula (5) below, a naturally sweet amino acid that is isolated and extracted from the roots of shrubs in Southern Africa. It has a potent sweet taste equivalent to several ten to several thousand times that of sucrose, and is expected to be useful as a sweetener. However, the usefulness of monatin has only been recently discovered, and a process for synthesizing monatin as the level of industrial production has yet to be established.

(5)

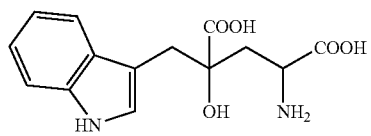

Under these circumstances, the inventors of the present invention developed a novel process for producing monatin composed of the following reactions (1) and (2) by using indole pyruvic acid and pyruvic acid which may be acquired as reagents.

(1) A reaction step of synthesizing precursor keto acid (IHOG) by aldol condensation of indole pyruvic acid and pyruvic acid (and/or oxalacetic acid); and,
(2) a reaction step of aminating the second position of IHOG

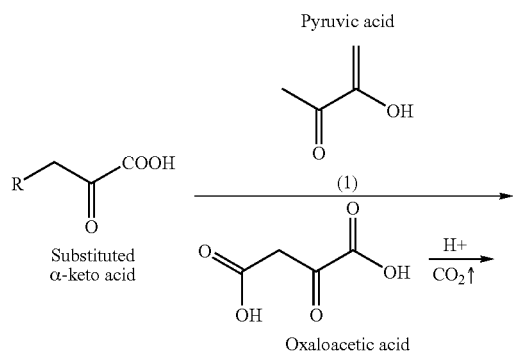

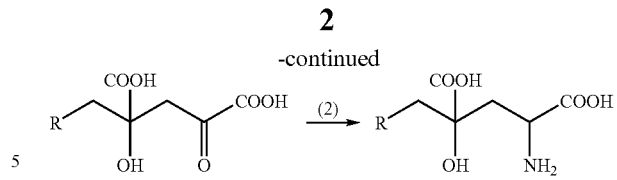

There have been no previous reports of examples of synthesizing precursor keto acid (IHOG) from indole pyruvic acid and pyruvic acid (or oxalacetic acid) using a microbial enzyme system for the aldol condensation reaction of (1) in the aforementioned synthesis route of monatin.

Examples of microbial enzymes that catalyze aldol condensation using two molecules of α-keto acid (or substituted α-keto acid) as a substrate reported thus far include 4-hydroxy-4-methyl-2-oxoglutarate aldolase derived from bacteria belonging to the genus *Pseudomonas*, and 4-hydroxy-2-oxoglutarate aldolase present in *E. coli*, *B. subtilis*, and so forth.

The former 4-hydroxy-4-methyl-2-oxoglutarate aldolase has been reported to catalyze a reaction in which 4-hydroxy-4-methyl-2-oxoglutarate (4-HMG) is formed from two molecules of pyruvic acid, and a reaction in which one molecule of oxalacetic acid and one molecule of pyruvic acid are formed from 4-oxalocitramalate (Kiyofumi Maruyama, Journal of Biochemistry, 108, 327-333 (1990)). Furthermore, the latter 4-hydroxy-2-oxoglutarate aldolase is known to catalyze a reaction in which 4-hydroxy-2-oxoglutarate (4HG) is formed from one molecule of glyoxylic acid and one molecule of pyruvic acid.

However, there have been no reports or findings indicating that any of these microorganisms are associated with activity that cleaves 4-phenylmethyl-4-hydroxy-2-oxoglutarate (PHOG) or activity that synthesizes a precursor keto acid (IHOG) of monatin from indole pyruvic acid and pyruvic acid (or oxalacetic acid), and whether or not the aldolases produced by these microbial strains may be used in the aforementioned synthesis route of monatin is unknown.

SUMMARY OF THE INVENTION

The object of the present invention is to provide an aldolase that may be appropriately used in the synthesis of IHOG, which is useful as an intermediate in the synthesis of monatin, and a process for producing substituted α-keto acids.

As a result of extensive research conducted in consideration of the aforementioned problems, the inventors of the present invention found that an aldolase that may be preferably used in the synthesis of the desired IHOG is present in certain microbial species, thereby leading to completion of the present invention.

Namely, the present invention is as described below.

[1] A DNA of following (a) or (b):
(a) A DNA comprising the nucleotide sequence of SEQ ID No: 1 or the nucleotide sequence of base numbers 444 to 1118 or base numbers 456 to 1118 of the same sequence;
(b) A DNA that hybridizes under stringent conditions with a DNA having a nucleotide sequence complementary to the nucleotide sequence of SEQ ID No: 1 or a nucleotide sequence of base numbers 444 to 1118 or 456 to 1118 of the same sequence, and encodes a protein having aldolase activity.

[2] A DNA of following (c) or (d):
(c) A DNA that encodes a protein comprising the amino acid sequence of SEQ ID No: 2 or an amino acid sequence of residue numbers 5 to 225 of the same sequence;

(d) A DNA that encodes a protein having an amino acid sequence that contains a substitution, deletion, insertion, addition or inversion of one or several amino acid residues in the amino acid sequence of SEQ ID No: 2 or an amino acid sequence of residue numbers 5 to 225 of the same sequence, and has aldolase activity.

[3] A DNA of following (e) or (f):
(e) A DNA comprising the nucleotide sequence of SEQ ID No: 15 or a nucleotide sequence of base numbers 398 to 1141 of the same sequence;
(f) A DNA that hybridizes under stringent conditions with a DNA having a nucleotide sequence complementary to the nucleotide sequence of SEQ ID No: 15 or a nucleotide sequence of base numbers 398 to 1141 of the same sequence, and encodes a protein having aldolase activity.

[4] A DNA of following (g) or (h):
(g) A DNA that encodes a protein comprising the amino acid sequence of SEQ ID No: 16;
(h) A DNA that encodes a protein having an amino acid sequence that contains a substitution, deletion, insertion, addition or inversion of one or several amino acid residues in the amino acid sequence of SEQ ID No: 16, and has aldolase activity.

[5] A recombinant DNA obtainable from ligating the DNA according to any of [1] to [4] with a vector DNA.

[6] A cell transformed by the recombinant DNA according to [5].

[7] A process for producing a protein having aldolase activity comprising: cultivating cells according to [6] in a medium, and accumulating a protein having aldolase activity in the any one of medium and cells or both.

[8] A protein of following (i) or (j):
(i) a protein comprising the amino acid sequence of SEQ ID No: 2 or an amino acid sequence of residue numbers 5 to 225 of the same sequence;
(j) a protein having an amino acid sequence that contains a substitution, deletion, insertion, addition or inversion of one or several amino acid residues in the amino acid sequence of SEQ ID No: 2 or an amino acid sequence of residue numbers 5 to 225 of the same sequence, and has aldolase activity.

[9] A protein of following (k) or (l):
(k) a protein comprising the amino acid sequence of SEQ ID No: 16;
(l) a protein having an amino acid sequence that contains a substitution, deletion, insertion, addition or inversion of one or several amino acid residues in the amino acid sequence of SEQ ID No: 16, and has aldolase activity.

[10] A protein which:
(A) has at least one of activities that catalyze reactions of:
4-(indol-3-ylmethyl)-4-hydroxy-2-oxoglutarate is formed by aldol condensation of indole-3-pyruvic acid and pyruvic acid, and
4-phenylmethyl-4-hydroxy-2-oxoglutarate is formed by aldol condensation of phenyl pyruvic acid and pyruvic acid,
(B) the optimum pH of the activity according to (A) is about 9 at 33° C., and
(C) the molecular weight as measured by gel filtration is about 146 kDa, and the molecular weight per subunit as measured by SDS-PAGE is about 25 kDa.

[11] A protein which:
(A) has aldolase activity,
(B) is derived from *Pseudomonas* species,
(C) has pH stability at pH 6 and above,
(D) has temperature stability at 70° C. or lower, and
(E) the molecular weight as measured by gel filtration is about 146 kDa, and the molecular weight per subunit as measured by SDS-PAGE is about 25 kDa.

[12] A protein according to [11], wherein the aldolase activity is improved by containing inorganic phosphate in the enzyme reaction mixture.

[13] A composition having aldolase activity obtainable from cultivating *Pseudomonas* species bacteria in a medium, accumulating any of the proteins of following (i) to (l) in any one of the medium and cells or both, and purifying any one of the medium and cells or both:
(i) a protein comprising the amino acid sequence of SEQ ID No: 2 or an amino acid sequence of residue numbers 5 to 225 of the same sequence;
(j) a protein having an amino acid sequence that contains a substitution, deletion, insertion, addition or inversion of one or several amino acid residues in the amino acid sequence of SEQ ID No: 2 or an amino acid sequence of residue numbers 5 to 225 of the same sequence, and has aldolase activity;
(k) a protein comprising the amino acid sequence of SEQ ID No: 16;
(l) a protein having an amino acid sequence that contains a substitution, deletion, insertion, addition or inversion of one or several amino acid residues in the amino acid sequence of SEQ ID No: 16, and has aldolase activity.

[14] A process for producing a substituted α-keto acid represented by the following general formula (3):

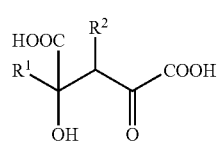

(3)

(wherein $R^1$ represents a hydrogen atom, an alkyl group having 1 to 8 carbon atoms, an alkoxyl group having 1 to 8 carbon atoms, a carboxyalkyl group having 2 to 9 carbon atoms, an aryl or an aralkyl group having up to 20 carbon atoms, a heterocycle-containing hydrocarbon group having up to 11 carbon atoms, a hydroxyl group or an ester derivative thereof, and $R^1$ may be substituted with at least one substituent selected from the group consisting of a halogen atom, a hydroxyl group, an alkyl group having up to 3 carbon atoms, an alkoxy group having up to 3 carbon atoms and an amino group; and $R^2$ represents a hydrogen atom, an alkyl group having 1 to 8 carbon atoms, an alkoxyl group having 1 to 8 carbon atoms, a carboxyalkyl group having 2 to 9 carbon atoms, an aryl or an aralkyl group having up to 20 carbon atoms, a heterocycle-containing hydrocarbon group having up to 11 carbon atoms, a hydroxyl group or an ester derivative thereof, and $R^2$ may be substituted with at least one substituent selected from the group consisting of a halogen atom, a hydroxyl group, an alkyl group having up to 3 carbon atoms, an alkoxy group having up to 3 carbon atoms and an amino group; and when $R^1$ represents a hydrogen atom, a methyl group or a carboxymethyl group in general formula (1), $R^2$ does not represent a hydrogen atom) comprising a reaction of the substituted α-keto acid represented by the following general formula (1):

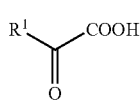

(wherein R¹ has the same meaning as R¹ in general formula (3)), with the substituted α-keto acid represented by the following general formula (2):

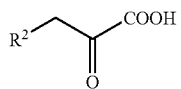

(wherein R² has the same meaning as defined in general formula (3));
wherein the reaction is performed in the presence of a protein that catalyzes the reaction.
[15] A process for producing a substituted α-keto acid according to [14], wherein R² represents a hydrogen atom or a carboxyl group.
[16] A process for producing a substituted α-keto acid according to [15], wherein R² represents a hydrogen atom.
[17] A process for producing a substituted α-keto acid according to [14], wherein R¹ represents a benzyl group or a 3-indolylmethyl group, and R² represents a hydrogen atom or a carboxyl group.
[18] A process for producing a substituted α-keto acid represented by the following formula (4):

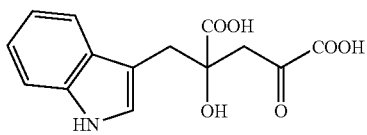

from oxalacetic acid or pyruvic acid, and indole-3-pyruvic acid wherein the reaction is performed in the presence of a protein that catalyzes the reaction.
[19] A process for producing a substituted α-keto acid according to [14] to [18], wherein the protein that catalyzes the reaction is derived from a microorganism selected from the group consisting of *Pseudomonas* species, *Erwinia* species, *Flavobacterium* species and *Xanthomonas* species.
[20] A process for producing a substituted α-keto acid according to [19], wherein the microorganism is *Pseudomonas taetrolens*, *Pseudomonas coronafaciens*, *Pseudomonas desmolytica*, *Erwinia* sp., *Flavobacterium rhenanum* or *Xanthomonas citri*.
[21] A process for producing a substituted α-keto acid according to [20], wherein the microorganism is *Pseudomonas taetrolens* ATCC4683 or *Pseudomonas coronafaciens* AJ2791.
[22] A process for producing a substituted α-keto acid according to [14] to [21], wherein the protein that catalyzes the reaction is a protein according to any of the following (i) to (l):
(i) a protein comprising the amino acid sequence of SEQ ID No: 2 or an amino acid sequence of residue numbers 5 to 225 of the same sequence;
(j) a protein having an amino acid sequence that contains a substitution, deletion, insertion, addition, or inversion of one or several amino acid residues in the amino acid sequence of SEQ ID No: 2 or an amino acid sequence of residue numbers 5 to 225 of the same sequence, and has aldolase activity;
(k) a protein comprising the amino acid sequence of SEQ ID No: 16;
(l) a protein having an amino acid sequence that contains a substitution, deletion, insertion, addition, or inversion of one or several amino acid residues in the amino acid sequence of SEQ ID No: 16, and has aldolase activity.
[23] A process for producing a substituted α-keto acid represented by the following general formula (3'):

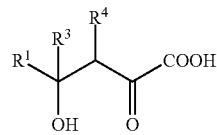

(wherein R¹ represents a hydrogen atom, an alkyl group having 1 to 8 carbon atoms, an alkoxyl group having 1 to 8 carbon atoms, a carboxyalkyl group having 2 to 9 carbon atoms, an aryl or an aralkyl group having up to 20 carbon atoms, a heterocycle-containing hydrocarbon group having up to 11 carbon atoms, a hydroxyl group or an ester derivative thereof, R³ represents a hydrogen atom or a carboxyl group, and R¹ may be substituted with at least one substituent selected from the group consisting of a halogen atom, a hydroxyl group, an alkyl group having up to 3 carbon atoms, an alkoxy group having up to 3 carbon atoms, and an amino group; and R⁴ represents a hydrogen atom, an alkyl group having 1 to 8 carbon atoms, an alkoxyl group having 1 to 8 carbon atoms, a carboxyalkyl group having 2 to 9 carbon atoms, an aryl or an aralkyl group having up to 20 carbon atoms, a heterocycle-containing hydrocarbon group having up to 11 carbon atoms, a hydroxyl group or an ester derivative thereof, and R⁴ may be substituted with at least one type of substituent selected from the group consisting of a halogen atom, a hydroxyl group, an alkyl group having up to 3 carbon atoms, an alkoxy group having up to 3 carbon atoms, and an amino group) comprising a reaction of the compound represented by the following general formula (1'):

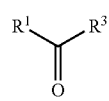

(wherein R¹ and R³ have the same meanings as defined in general formula (3')), with the substituted α-keto acid represented by the following general formula (2'):

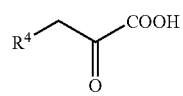

(wherein R⁴ has the same meaning as defined in general formula (3'));

wherein the reaction is performed in the presence of a protein according to [8] or [9].

[24] A process for producing a substituted α-keto acid according to [23], wherein R⁴ is a hydrogen atom or a carboxyl group.

DETAILED DESCRIPTION OF THE INVENTION

Figure 1:
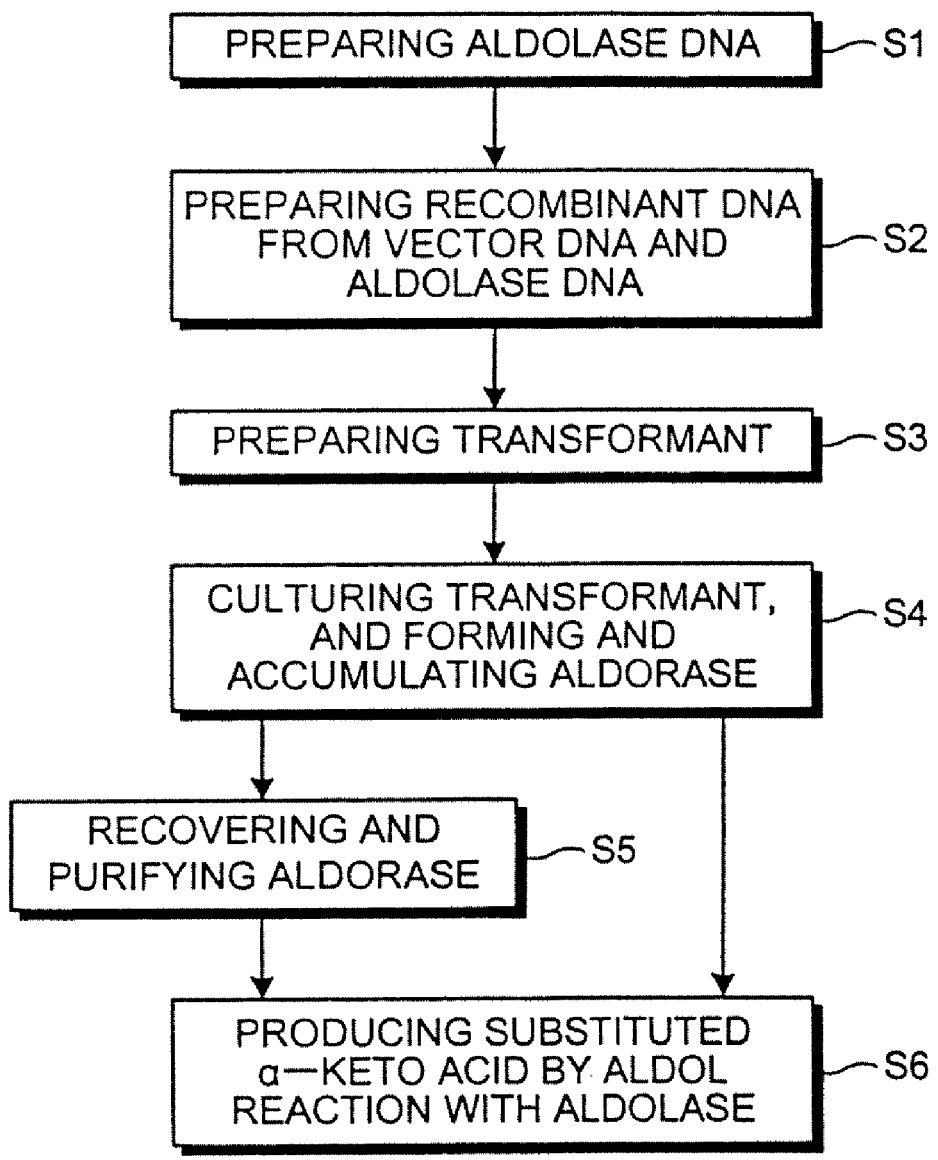
FIG. 1 shows a flowchart of the process for producing aldolase of the present invention.

The following provides a detailed explanation of [I] aldolase and [II] a process for producing substituted α-keto acid using aldolase of the present invention with reference to the accompanying drawings.

[I] Aldolase

According to research by the inventors of the present invention, bacterial strains were confirmed to exist that form aldolase having the ability to cleave 4-phenylmethyl-4-hydroxy-2-oxoglutarate (PHOG) in the genus *Pseudomonas, Erwinia, Flavobacterium*, and *Xanthomonas*.

Since the aldolase produced by these microorganisms catalyzes a reaction that forms one molecule of phenyl pyruvic acid and one mole of pyruvic acid by cleaving one molecule of PHOG, the inventors of the present invention thought that the aldolase could catalyze a reaction in which 4-(indol-3-ylmethyl)-4-hydroxy-2-oxoglutarate (IHOG) is formed from indole pyruvic acid and pyruvic acid (or oxalacetic acid). On the basis of this approach, in order to clarify the existence of a novel aldolase, together with purifying and isolating aldolase from cultivated microbial cells of the microorganisms, the inventors of the present invention found that this enzyme synthesizes IHOG by aldol condensation of indole pyruvic acid and pyruvic acid (or oxalacetic acid).

Furthermore, the inventors of the present invention determined the amino acid sequence of the aldolase by purifying aldolase derived from *Pseudomonas taetrolens* ATCC4638 (which may also be abbreviated as PtALD). Furthermore, the inventors of the present invention also synthesized a DNA molecule of about 30 base pairs deduced from the amino acid sequence of the aldolase, isolated and obtained a fragment of DNA that encodes the aldolase by PCR using this DNA molecule, and succeeded in isolating the entire length of DNA that encodes PtALD from a chromosome library of this microorganism by using the DNA fragment as a probe.

The DNA that encodes the PtALD of the present invention that is identified according to the aforementioned method is shown in SEQ ID No: 1 in the Sequence Listing. Furthermore, the amino acid sequence of PtALD encoded by the nucleotide sequence of SEQ ID No: 1 is shown in SEQ ID No: 2 and SEQ ID No: 3. SEQ ID No: 2 is the amino acid sequence of PtALD encoded by the nucleotide sequence of base numbers 456 to 1118 in the nucleotide sequence of SEQ ID No: 1. Furthermore, SEQ ID No: 3 is the amino acid sequence of PtALD encoded by the nucleotide sequence of base numbers 444 to 1118 in the nucleotide sequence of SEQ ID No: 1, and is equivalent to the amino acid sequence of residue numbers 5 to 225 in the amino acid sequence of SEQ ID No: 2. Both of the PtALD of SEQ ID No: 2 and SEQ ID No: 3 have aldolase activity, and catalyze the reaction in which 4-(indol-3-ylmethyl)-4-hydroxy-2-oxoglutarate (IHOG) shown in the following formula (4) is synthesized from one molecule of indole pyruvic acid and one molecule of oxalacetic acid (or pyruvic acid).

Furthermore, the inventors of the present invention also succeeded in isolating the entire length of DNA that encodes aldolase derived from *Pseudomonas coronafaciens* ATCC4683 (which may also be abbreviated as PcALD) from a chromosomal DNA library of the microorganism by using an obtained DNA fragment that encodes PtALD as a probe. A DNA that encodes the PcALD of the present invention identified by the aforementioned method is shown in SEQ ID No: 15. The amino acid sequence of PcALD encoded by the nucleotide sequence of SEQ ID No: 15 is shown in SEQ ID No: 16. SEQ ID No: 16 is an amino acid sequence of PcALD encoded by the nucleotide sequence of base numbers 398 to 1141 of the nucleotide sequence of SEQ ID No: 15. The PcALD of SEQ ID No: 16 also has aldolase activity and catalyzes the reaction in which 4-(indol-3-ylmethyl)-4-hydroxy-2-oxoglutarate (IHOG) shown in the following formula (4) is synthesized from one molecule of indole pyruvic acid and one molecule of oxalacetic acid (or pyruvic acid).

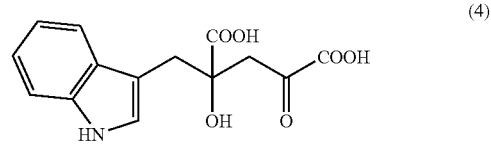

(4)

Next, a detailed explanation is provided of (1) a DNA encoding aldolase, (2) properties of aldolase and (3) a process for producing aldolase in that order.

(1) A DNA Encoding Aldolase

The aldolase gene of the present invention having the nucleotide sequence of SEQ ID No: 1 was isolated from a chromosomal DNA of *Pseudomonas taetrolens* strain ATCC4683 as described above. The nucleotide sequence of SEQ ID No: 1 demonstrates homology of 29% with known 4-hydroxy-4-methyl-2-oxoglutarate aldolase (gene name: proA) (Biosci. Biotechnol. Biochem., 65(12), 2701-2709 (2001), Maruyama, K. et al.) derived from the bacterium, *Pseudomonas ochraceae*, at the amino acid sequence level.

The aldolase gene of the present invention having the nucleotide sequence of SEQ ID No: 15 was isolated from a chromosomal DNA of *Pseudomonas coronafaciens* strain AJ2791 as described above. The amino acid sequence encoded by the nucleotide sequence of SEQ ID No: 15 demonstrates homology of 28% with known 4-hydroxy-4-methyl-2-oxoglutarate aldolase (gene name: proA) (Biosci. Biotechnol. Biochem., 65(12), 2701-2709 (2001), Maruyama, K. et al.) derived from the bacterium, *Pseudomonas ochraceae*. Furthermore, the amino acid sequence encoded by the nucleotide sequence of SEQ ID No: 15 demonstrates homology of 41% with the aldolase derived from the strain *Pseudomonas taetrolens* ATCC 4683 described above.

Here, analysis of homology indicates the value obtained by calculating the parameter as the initial set value using the "Genetyx Ver. 6" genetic analytical software (Genetyx).

The following provides an explanation of the method for obtaining a DNA encoding aldolase from aldolase-producing bacteria.

First, the amino acid sequence of the purified aldolase is determined. At this time, the amino acid sequence may be determined by using the method of Edman (Edman, P., Acta Chem. Scand. 4, 227 (1950)). Furthermore, the amino acid sequence may be determined using the Sequencer made by Applied Biosystems. Following limited hydrolysis with protease of the aldolase of the present invention derived from *Pseudomonas taetrolens* strain ATCC4683, peptide fragments were fractionated with reverse phase HPLC. Determination of the internal amino acid sequences of two of these fragments clearly revealed them to be the sequences shown in SEQ ID No: 4 and SEQ ID No: 5.

The nucleotide sequence of a DNA that encodes these amino acid sequences is then able to be deduced based on the amino acid sequences that are determined. Universal codons are employed to deduce the nucleotide sequence of the DNA.

DNA molecules of about 30 base pairs were then synthesized based on the deduced nucleotide sequence. The method used to synthesize the DNA molecules is disclosed in Tetrahedron Letters, 22, 1859 (1981). Furthermore, the DNA molecules may also be synthesized using the Synthesizer made by Applied Biosystems. The DNA molecules may be used as a probe when isolating the entire length of DNA that encodes aldolase from a chromosomal DNA library of a microorganism that produces aldolase. Alternatively, they may also be used as a primer when amplifying a DNA that encodes aldolase of the present invention by PCR. However, since the DNA amplified using PCR does not contain the entire length of DNA that encodes aldolase, the entire length of DNA that encodes aldolase is isolated from a chromosomal DNA library of a microorganism that produces aldolase using the DNA amplified by PCR as a probe.

The procedure employed for PCR is described in publications such as White, T J. et al., Trends Genet. 5, 185 (1989). The method for isolating a chromosomal DNA, as well as the method for isolating a desired DNA molecule from a gene library using a DNA molecule as a probe, are described in publications such as Molecular Cloning, 2nd edition, Cold Spring Harbor Press (1989).

A method for determining the nucleotide sequence of isolated a DNA that encodes aldolase is described in A Practical Guide to Molecular Cloning, John Wiley & Sons, Inc. (1985). Furthermore, the nucleotide sequence may be determined by using the DNA Sequencer made by Applied Biosystems. A DNA encoding aldolase derived from *Pseudomonas taetrolens* strain ATCC4683 is shown in SEQ ID No: 1, while a DNA encoding aldolase derived from *Pseudomonas coronafaciens* strain AJ2791 is shown in SEQ ID No:

A DNA that encodes aldolase which catalyzes the reaction in which IHOG is formed from indole pyruvic acid and pyruvic acid (or oxalacetic acid) is not only the DNA shown in SEQ ID Nos: 1 and 15. This is because there ought to be differences in nucleotide sequences observed for each species and strain among *Pseudomonas* species that form aldolase which catalyzes the reaction in which IHOG is synthesized from indole pyruvic acid and pyruvic acid (or oxalacetic acid).

The DNA of the present invention not only includes the isolated DNA that encodes aldolase, but a DNA in which mutations have been artificially added to a DNA that encodes aldolase isolated from a chromosomal DNA of an aldolase-producing microorganism is also included in the DNA of the present invention when it encodes aldolase. Methods for artificially adding mutations include commonly used methods such as the method for introducing site-specific mutations described in Method. in Enzymol., 154 (1987).

A DNA that hybridizes under stringent conditions with a DNA having a nucleotide sequence complementary to the nucleotide sequence of SEQ ID No: 1, and encodes a protein having aldolase activity is also included in the DNA of the present invention. As used herein, the "stringent conditions" refer to those conditions under which a specific hybrid is formed whereas an unspecific hybrid is not formed. Although it is difficult to numerically express these conditions explicitly, by way of example, mention is made of those conditions under which DNA molecules having higher homology e.g. preferably 50% or more, more preferably 80% or more, still more preferably 90% or more, and particularly preferably 95% or more homology, hybridize with each other, while DNA molecules having lower homology do not hybridize with each other, or those conditions under which hybridization occurs under usual washing conditions in Southern hybridization, that is, at a salt concentration corresponding to 0.1×SSC and 0.1% SDS at 37° C., preferably 0.1×SSC and 0.1% SDS at 60° C., and more preferably 0.1×SSC and 0.1% SDS at 65° C. Furthermore, "aldolase activity" may be sufficient for the activity that synthesizes IHOG from indole pyruvic acid and pyruvic acid (or oxalacetic acid). However, in the case of a nucleotide sequence that hybridizes under stringent conditions with a nucleotide sequence complementary to the nucleotide sequence of SEQ ID No: 1, it preferably retains aldolase activity of 10% or more, preferably 30% or more, more preferably 50% or more, and still more preferably 70% or more, of protein having the amino acid sequence of SEQ ID No: 2 or 3 under conditions of 33° C. and pH9.

A DNA that hybridizes under stringent conditions with a DNA having a nucleotide sequence complementary to the nucleotide sequence of SEQ ID No: 15, and encodes a protein having aldolase activity is also included in the DNA of the present invention. As used herein, the "stringent conditions" refer to those conditions under which a specific hybrid is formed whereas an unspecific hybrid is not formed. Although it is difficult to numerically express these conditions explicitly, by way of example, mention is made of those conditions under which DNA molecules having higher homology e.g. preferably 50% or more, more preferably 80% or more, still more preferably 90% or more, and particularly preferably 95% or more homology, hybridize with each other, while DNA molecules having lower homology do not hybridize with each other, or those conditions under which hybridization occurs under usual washing conditions in Southern hybridization, that is, at a salt concentration corresponding to 0.1×SSC and 0.1% SDS at 37° C., preferably 0.1×SSC and 0.1% SDS at 60° C., and more preferably 0.1×SSC and 0.1% SDS at 65° C. Furthermore, "aldolase activity" may be sufficient for the activity that synthesizes IHOG from indole pyruvic acid and pyruvic acid (or oxalacetic acid). However, in the case of a nucleotide sequence that hybridizes under stringent conditions with a nucleotide sequence complementary to the nucleotide sequence of SEQ ID No: 15, it preferably retains aldolase activity of 10% or more, preferably 30% or more, more preferably 50% or more, and still more preferably 70% or more, of protein having the amino acid sequence of SEQ ID No: 16 under conditions of 33° C. and pH 9.

Furthermore, a DNA that encodes a protein which is substantially identical to the aldolase encoded by the DNA of SEQ ID No: 1 or 15 is also included in the DNA of the present invention. Namely, the following DNAs are also included in the DNA of the present invention:

(a) a DNA comprising the nucleotide sequence of base numbers 444 to 1118 or 456-1118 in the nucleotide sequence of SEQ ID No: 1;
(b) a DNA that hybridizes under stringent conditions with a DNA having a nucleotide sequence complementary to the nucleotide sequence of base numbers 444 to 1118 or 456 to 1118 in the nucleotide sequence of SEQ ID No: 1, and encodes a protein having aldolase activity;
(c) a DNA that encodes a protein comprising the amino acid sequence of SEQ ID No: 2 or an amino acid sequence of residue numbers 5 to 225 of the same sequence;
(d) a DNA that encodes a protein having an amino acid sequence that contains a substitution, deletion, insertion, addition or inversion of one or several amino acid residues in the amino acid sequence of SEQ ID No: 2 or an amino acid sequence of residue numbers 5 to 225 of the same sequence, and has aldolase activity;
(e) a DNA comprising the nucleotide sequence of base numbers 398 to 1141 in the nucleotide sequence of SEQ ID No: 15;
(f) a DNA that hybridizes under stringent conditions with a DNA having a nucleotide sequence complementary to the nucleotide sequence of base numbers 398 to 1141 in the nucleotide sequence of SEQ ID No: 15, and encodes a protein having aldolase activity;
(g) a DNA that encodes a protein comprising the amino acid sequence of SEQ ID No: 16; and,
(h) a DNA that encodes a protein having an amino acid sequence that contains a substitution, deletion, insertion, addition or inversion of one or several amino acid residues in the amino acid sequence of SEQ ID No: 16, and has aldolase activity. Here, "one or several" refers to the range over which the steric structure of a protein of amino acid residues or aldolase activity is not significantly impaired, and more specifically, a range of 1 to 50, preferably 1 to 30 and more preferably 1 to 10. Furthermore, "aldolase activity" refers to the activity that synthesizes IHOG from indole pyruvic acid and pyruvic acid (or oxalacetic acid) as described above. However, in the case of an amino acid sequence that contains a substitution, deletion, insertion, addition or inversion of one or several amino acid residues in the amino acid sequence of SEQ ID No: 2, 3, or 16, it preferably retains aldolase activity of 10% or more, preferably 30% or more, more preferably 50% or more, and still more preferably 70% or more, of protein having the amino acid sequence of SEQ ID No: 2, 3, or 16 under conditions of 33° C. and pH 9.

(2) Properties of Aldolase

Next, an explanation is provided of the properties of purified aldolase derived from *Pseudomonas taetrolens* strain ATCC4683 (PtALD) and purified aldolase derived from *Pseudomonas coronafaciens* strain AJ2791 (PcALD).

The PtALD of the present invention has the amino acid sequence of SEQ ID No: 2 or 3 as is clearly determined by the previously described gene isolation and analysis. However, the present invention includes a protein having an amino acid sequence that contains a substitution, deletion, insertion, addition or inversion of one or several amino acid residues in the amino acid sequence of SEQ ID No: 2 or 3, which also has aldolase activity.

The PcALD of the present invention has the amino acid sequence of SEQ ID No: 16 as is clearly determined by the previously described gene isolation and analysis. However, the present invention includes a protein having an amino acid sequence that contains a substitution, deletion, insertion, addition or inversion of one or several amino acid residues in the amino acid sequence of SEQ ID No: 16, which also has aldolase activity.

Namely, the aldolase of the present invention consists of the proteins indicated in (i) to (l) below.

(i) a protein comprising the amino acid sequence of SEQ ID No: 2 or an amino acid sequence of residue numbers 5 to 225 of the same sequence;
(j) a protein having an amino acid sequence that contains a substitution, deletion, insertion, addition or inversion of one or a several amino acid residues in the amino acid sequence of SEQ ID No: 2 or an amino acid sequence of residue numbers 5 to 225 in the same sequence, and has aldolase activity;
(k) a protein comprising the amino acid sequence of SEQ ID No: 16; and,
(l) a protein having an amino acid sequence that contains a substitution, deletion, insertion, addition or inversion of one or several amino acid residues in the amino acid sequence of SEQ ID No: 16, and has aldolase activity.

Here, the definitions of "several" and "aldolase activity" are the same as defined in section (1), DNA Encoding Aldolase.

The aldolase of the present invention catalyzes the reaction that synthesizes 4-(indol-3-ylmethyl)-4-hydroxy-2-oxoglutarate (IHOG) by aldol condensation from indole pyruvic acid and pyruvic acid (or oxalacetic acid).

The aldolase activity of the aldolase of the present invention may be measured by measuring the amount of IHOG formed from indole pyruvic acid and pyruvic acid (or oxalacetic acid) by high-performance liquid chromatography (HPLC).

More specifically, aldolase activity may be estimated according to the following steps of adding aldolase to a reaction solution composed of 100 mM buffer, 50 mM indole-3-pyruvic acid, 250 mM pyruvic acid, 1 mM $MgCl_2$ and 1% (v/v) toluene; and shaking while reaction at 33° C. for 4 hours; and then quantifying the amount of IHOG formed by HPLC.

IHOG may be quantified by HPLC analysis using the "Inertsil ODS-2" (GL Sciences Inc., 5 μm, 4.6×250 mm). The following indicates an example of the analysis conditions.

Mobile phase: 40% (v/v) acetonitrile/5 mM dihydrogen phosphate tetrabutyl ammonium solution
Flow rate: 1 ml/min
Column temperature: 40° C.
Detection: UV 210 nm The aldolase of the present invention is able to catalyze the reaction that synthesizes IHOG by aldol condensation from indole pyruvic acid and pyruvic acid (or oxalacetic acid). Although two examples of microbial enzymes capable of catalyzing aldol condensation using 2 molecules of α-keto acid (or substituted α-keto acid) as a substrate have been reported thus far consisting of 4-hydroxy-4-methyl-2-oxoglutarate aldolase derived from *Pseudomonas* species bacteria and 4-hydroxy-2-oxoglutarate aldolase present in microorganisms such as *E. coli* and *B. subtilis*, there have been no findings or reports describing the former acting on PHOG or IHOG, and it is completely unknown as to whether it is possible to synthesize PHOG (and IHOG) by using this enzyme. Furthermore, PHOG cleaving activity has not been observed for the latter, and it has not been possible to synthesize PHOG (and IHOG) using this enzyme as well. Namely, the aldolase of the present invention differs from aldolases that have been reported thus far in that it has the characteristic of being able to catalyze the reaction in which IHOG is synthesized by aldol condensation of indole pyruvic acid and pyruvic acid (or oxalacetic acid).

Next, the following provides a description of the enzymatic properties investigated for purified PtALD.

PtALD catalyzes the reaction that forms a substituted α-keto acid represented by the following general formula (3'):

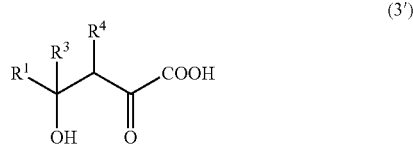

(wherein $R^1$ represents a hydrogen atom, an alkyl group having 1 to 8 carbon atoms, an alkoxyl group having 1 to 8 carbon atoms, a carboxyalkyl group having 2 to 9 carbon atoms, an aryl or an aralkyl group having up to 20 carbon atoms, a heterocycle-containing hydrocarbon group having up to 11 carbon atoms, a hydroxyl group or an ester derivative thereof; $R^3$ represents a hydrogen atom or a carboxyl group, and $R^1$ may be substituted with at least one substituent selected from the group consisting of a halogen atom, a hydroxyl group, an alkyl group having up to 3 carbon atoms, an alkoxy group having up to 3 carbon atoms and an amino group; and $R^4$ represents a hydrogen atom, an alkyl group having 1 to 8 carbon atoms, an alkoxyl group having 1 to 8 carbon atoms, a carboxyalkyl group having 2 to 9 carbon atoms, an aryl or an aralkyl group having up to 20 carbon atoms, a heterocycle-containing hydrocarbon group having up to 11 carbon atoms, a hydroxyl group or an ester derivative thereof, and $R^4$ may be substituted with at least one substituent selected from the group consisting of a halogen atom, a hydroxyl group, an alkyl group having up to 3 carbon atoms, an alkoxy group having up to 3 carbon atoms and an amino group) from the compound represented by the following general formula (1'):

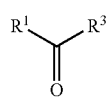

(wherein $R^1$ and $R^3$ has the same meaning as defined in general formula (3')), and the substituted α-keto acid represented by the following general formula (2'):

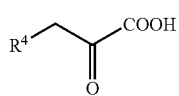

(wherein $R^4$ has the same meaning as defined in general formula (3')). Thus, a process whereby the compound of general formula (3') is produced from the compounds of general formula (1') and general formula (2') by using the PtALD of the present invention also belongs to the present invention. Here, $R^4$ is preferably a hydrogen atom or a carboxyl group.

The optimum pH of PtALD is nearly about 9 at 33° C. Furthermore, the PtALD of the present invention has pH stability at pH 6 or higher, and has particularly high pH stability within the range of pH 6 to pH 11. Furthermore, the PtALD of the present invention has temperature stability at 70° C. or lower, and has particularly high temperature stability within the range of 20 to 60° C. Furthermore, the PtALD of the present invention has the property of aldolase activity being improved by addition of inorganic phosphoric acid such as KPi to the enzyme reaction mixture.

Since the molecular weight of PtALD is about 146 kDa as measured by gel filtration and about 25 kDa as measured by SDS-PAGE, It was suggested that PtALD has a hexameric structure consisting of six subunits having a molecular weight of about 25 kDa.

(3) Process for Producing Aldolase

Next, an explanation is provided for the process of producing the aldolase of the present invention. There are two ways to produce the aldolase of the present invention. These consist of (i) a process of cultivating an aldolase-producing microorganism to form and accumulate aldolase, and (ii) a process of preparing a transformant to form aldolase by a recombinant DNA technology and cultivating the transformant to accumulate aldolase.

(i) Process for Forming and Accumulating Aldolase by Microbial Cultivation

Examples of microorganisms serving as acquisition sources of aldolase in a process for forming and accumulating aldolase by cultivating aldolase-producing microorganisms include microorganisms belonging to the genus *Pseudomonas, Erwinia, Flavobacterium*, and *Xanthomonas*.

Any microorganisms belonging to the genus *Pseudomonas, Erwinia, Flavobacterium*, or *Xanthomonas* may be used in the present invention provided they are microorganisms that form aldolase which catalyzes a reaction that synthesizes a precursor keto acid (IHOG) from indole pyruvic acid and pyruvic acid (or oxalacetic acid), and preferable microorganisms include *Pseudomonas taetrolens* ATCC4683, *Pseudomonas coronafaciens* AJ2791, *Pseudomonas desmolytica* AJ1582, *Erwinia* sp. AJ2917, *Xanthomonas citri* AJ2797 and *Flavobacterium rhenanum* AJ2468 is used preferably. Among these, *Pseudomonas taetrolens* ATCC4683 and *Pseudomonas coronafaciens* AJ2791 are particularly preferable. The locations where these microorganisms are deposited are indicated below.

(1) *Pseudomonas coronafaciens* Strain AJ2791
  (i) Deposit no.: FERM BP-8246 (transferred from FERM P-18881)
  (ii) Deposition date: Jun. 10, 2002
  (iii) Deposited location: National Institute of Advanced Industrial Science and Technology, International Patent Organism Depository (Chuo No. 6, 1-1-1 Higashi, Tsukuba City, Ibaraki Prefecture, Japan)

(2) *Pseudomonas desmolytica* Strain AJ1582
  (i) Deposit no.: FERM BP-8247 (transferred from FERM P-18882)
  (ii) Deposition date: Jun. 10, 2002
  (iii) Deposited location: National Institute of Advanced Industrial Science and Technology, International Patent Organism Depository (Chuo No. 6, 1-1-1 Higashi, Tsukuba City, Ibaraki Prefecture, Japan)

(3) *Erwinia* sp. Strain AJ2917
  (i) Deposit no.: FERM BP-8245 (transferred from FERM P-18880)
  (ii) Deposition date: Jun. 10, 2002
  (iii) Deposited location: National Institute of Advanced Industrial Science and Technology, International Patent Organism Depository (Chuo No. 6, 1-1-1 Higashi, Tsukuba City, Ibaraki Prefecture, Japan)

(4) *Flavobacterium rhenanum* Strain AJ2468
  (i) Deposit no.: FERM BP-1862
  (ii) Deposition date: Sep. 30, 1985

(iii) Deposited location: National Institute of Advanced Industrial Science and Technology, International Patent Organism Depository (Chuo No. 6, 1-1-1 Higashi, Tsukuba City, Ibaraki Prefecture, Japan)

(5) *Xanthomonas citri* Strain AJ2797

(i) Deposit no.: FERM BP-8250 (transferred from FERM P-8462)

(ii) Deposition date: Sep. 30, 1985

(iii) Deposited location: National Institute of Advanced Industrial Science and Technology, International Patent Organism Depository (Chuo No. 6, 1-1-1 Higashi, Tsukuba City, Ibaraki Prefecture, Japan)

Although the microorganism serving as the acquisition source of aldolase may be cultivated in any form such as liquid cultivation and solid cultivation, an industrially advantageous method is deep-aerated stir cultivation. Carbon sources, nitrogen sources, inorganic salts, and other trace nutrient elements commonly used in microbial cultivating may be used as nutrient elements of nutritive media. All nutrient sources may be used provided they may be used by the microbial strain being used.

Aerobic conditions are used for the aeration conditions. The cultivating temperature may be sufficient within a range in which the microorganisms grow and aldolase is produced. Thus, although the conditions are not strict, the cultivating temperature is normally 10 to 50° C. and preferably 30 to 40° C. The cultivating time varies according to other cultivating conditions. For example, the microorganisms may be cultivated until the greatest amount of aldolase is produced, and this is normally about 5 hours to 7 days, and preferably about 10 hours to 3 days.

Following cultivation, the microbial cells are recovered by centrifugation (e.g., 10,000×g for 10 minutes). Since the majority of the aldolase is present in the cells, the aldolase is solubilized by disrupting or lysing the microbial cells. Ultrasonic disrupting, French press disrupting or glass bead disrupting may be used to disrupt the microbial cells. In the case of lysing the cells, a method that uses egg white lysozyme, peptidase treatment, or a suitable combination thereof is adopted.

When aldolase derived from an aldolase-producing microorganism is purified, although the aldolase is purified by using an enzyme solubilizing solution for the starting material, if undisrupted or unlysed residue remains, re-centrifuging the solubilization solution and removing any residue that precipitates is advantageous to purification.

All commonly used methods for purifying ordinary enzymes may be employed to purify the aldolase, examples of which include ammonium sulfate salting-out, gel filtration chromatography, ion exchange chromatography, hydrophobic chromatography and hydroxyapatite chromatography. As a result, an aldolase-containing fraction with higher specific activity may be obtained having higher specific activity.

(ii) Production Process Using Recombinant DNA Technology

Next, an explanation is provided for a process for producing aldolase using a recombinant DNA technology. There are numerous known examples of producing useful proteins such as enzymes and physiologically active substances using a recombinant DNA technology, and the use of recombinant DNA technology enables mass production of useful proteins present only in trace amounts in nature.

FIG. 1 is a flowchart of a process for producing the aldolase of the present invention.

First, a DNA is prepared that encodes the aldolase of the present invention (Step S1).

Next, the prepared DNA is ligated with a vector DNA to produce a recombinant DNA (Step S2), and cells are transformed by the recombinant DNA to produce a transformant (Step S3). Continuing, the transformant is cultivated in a medium, and the aldolase is allowed to form and accumulate in any one of the medium and cells or both (Step S4).

Subsequently, the process proceeds to Step S5 where purified aldolase is produced by recovering and purifying the enzyme.

The desired substituted α-keto acid may be produced in a large amount by using the purified aldolase produced at Step S5 or any of the medium and cells or both in which aldolase has accumulated at Step S4 in an aldol reaction (Step S6).

The DNA that is ligated with the vector DNA may allow expression of the aldolase of the present invention.

Here, examples of aldolase genes ligated into the vector DNA include the previously described DNA indicated below:

(a) a DNA comprising the nucleotide sequence of SEQ ID No: 1, or the nucleotide sequence of base numbers 444 to 1118 or base numbers 456 to 1118 in the same sequence;

(b) a DNA that hybridizes under stringent conditions with a DNA having a nucleotide sequence complementary to the nucleotide sequence of SEQ ID No: 1 or a nucleotide sequence of base numbers 444 to 1118 or 456 to 1118 of the same sequence, and encodes a protein having aldolase activity;

(c) a DNA that encodes a protein comprising the amino acid sequence of SEQ ID No: 2 or an amino acid sequence of residue numbers 5 to 225 of the same sequence;

(d) a DNA that encodes a protein having an amino acid sequence that contains a substitution, deletion, insertion, addition or inversion of one or several amino acid residues in the amino acid sequence of SEQ ID No: 2 or an amino acid sequence of residue numbers 5 to 225 of the same sequence, and has aldolase activity;

(e) a DNA comprising the nucleotide sequence of SEQ ID No: 15, or a nucleotide sequence of base numbers 398 to 1141 of the same sequence;

(f) a DNA that hybridizes under stringent conditions with a DNA having a nucleotide sequence complementary to the nucleotide sequence of SEQ ID No: 15 or a nucleotide sequence of base numbers 398 to 1141 of the same sequence, and encodes a protein having aldolase activity;

(g) a DNA that encodes a protein comprising the amino acid sequence of SEQ ID No: 16; and, (h) a DNA that encodes a protein having an amino acid sequence that contains a substitution, deletion, insertion, addition, or inversion of one or several amino acid residues in the amino acid sequence of SEQ ID No: 16, and has aldolase activity.

In the case of mass production of protein using recombinant DNA technology, it is preferable to form a inclusion body of protein by associating the protein within a transformant that produces the protein. The advantages of this expression production method include being able to protect the desired protein from digestion by proteases present within microbial cells, and being able to easily purify the desired protein by a centrifugation procedure after disrupting the microbial cells.

Protein inclusion bodies that have been obtained in this manner are solubilized by a protein denaturant, and after going through a renaturing procedure consisting primarily of removing the denaturant, such protein is converted to properly folded, physiologically active protein. There are numerous examples of this such as the restoration of the activity of human interleukin-2 (JP-A-S61-257931).

In order to obtain a active protein from a inclusion body of protein, a series of procedures including solubilization and restoration of activity are required, and these procedures are more complex than producing the active protein directly. However, in the case of large scale production in microbial cells of a protein that affects microbial growth, those effects may be inhibited by allowing the protein to accumulate within the microbial cells in the form of inactive inclusion bodies.

Methods for mass production of a desired protein in the form of inclusion bodies include a method in which the desired protein is expressed independently under the control of a powerful promoter, and a method in which the desired protein is expressed as a fused protein with a protein that is known to be expressed in large scale.

Furthermore, it is also effective to arrange the recognition sequence of a restricting protease at a suitable location in order to cut out the desired protein after having expressed in the form of a fused protein.

In the case of large scale protein production using recombinant DNA technology, cells such as bacterial cells, *Actinomyces* cells, yeast cells, mold cells, plant cells and animal cells may be used for the host cells that are transformed. Examples of bacterial cells for which host-vector systems have been developed include *Escherichia* species, *Pseudomonas* species, *Corynebacterium* species, and *Bacillus* species, and preferably *Escherichia coli* is used. This is because there are numerous knowledge regarding technologies for mass production of protein using *Escherichia coli*. The following provides an explanation of a process for producing aldolase using transformed *E. coli*.

A promoter normally used for heterogeneous protein production in *E. coli* may be used for the promoter that expresses a DNA encoding aldolase, examples of which include powerful promoters such as T7 promoter, trp promoter, lac promoter, tac promoter and PL promoter.

In order to produce aldolase in the form of a fused protein inclusion body, a gene that encodes another protein, preferably a hydrophilic peptide, is ligated either upstream or downstream of the aldolase gene with a fused protein gene. The gene that encodes another protein may be a gene that increases the amount of fused protein accumulated and enhances the solubility of the fused protein following the denaturation and regeneration steps, examples of candidates for which include T7 gene 10, β-galactosidase gene, dehydrofolate reductase gene, interferon-γ gene, interleukin-2 gene and prochymosin gene.

When ligating these genes with a gene that encodes aldolase, the codon reading frames are made to match. The genes may either be ligated in a suitable restriction enzyme site or using a synthetic DNA of an appropriate sequence.

In order to increase the amount produced, it is preferable to couple a transcription terminating sequence in the form of a terminator downstream from the fused protein gene. Examples of this terminator include T7 terminator, fd phage terminator, T4 terminator, tetracycline resistance gene terminator, and *E. coli* trpA gene terminator.

Multi-copy vectors are preferable for the vector used to introduce a gene that encodes aldolase or a fused protein of aldolase with another protein into *E. coli*, examples of which include plasmids having a replication starting point derived from Col E1 such as pUC plasmids, pBR322 plasmids or their derivatives. A "derivative" here refers to that has undergone alteration of a plasmid by base substitution, deletion, insertion, addition or inversion. The alteration referred to here includes alteration caused by mutagenic treatment using a mutagen or UV irradiation or by spontaneous mutation.

It is preferable that the vector has a marker such as ampicillin resistance gene in order to select the transformant. Examples of such plasmids include commercially available expression vectors having a powerful promoter (such as pUC (Takara), pPROK (Clontech), and pKK233-2 (Clontech)).

A recombinant DNA is obtainable from ligating a DNA fragment, in which a promoter, a gene encoding aldolase or fused protein consisting of aldolase and another protein, and a terminator are ligated in that order, with a vector DNA.

When *E. coli* is transformed using the recombinant DNA and that *E. coli* is then cultivated, aldolase or a fused protein of aldolase with another protein is expressed and produced. A strain that is normally used for expression of heterogeneous genes may be used for the transformed host, and *E. coli* strain JM109(DE3) and *E. coli* strain JM109 are particularly preferable. The transformation method and method for selecting the transformant are described in, for example, Molecular Cloning, 2nd edition, Cold Spring Harbor Press (1989).

In the case of expressing as fused protein, the aldolase may be cut out using a restricting protease such as blood coagulation factor Xa or kallikrein that recognizes sequences not existing in aldolase as the recognition sequence.

A medium normally used for cultivating *E. coli* may be used for the production medium, examples of which include M9-casamino acid medium and LB medium. Furthermore, conditions of cultivating and production induction may be appropriately selected according to the type of the marker and promoter of the vector used, and type of host microorganism used.

The following method may be used to recover the aldolase or fused protein of aldolase with another protein. If the aldolase or its fused protein is solubilized within microbial cells, then it may be used in the form of a crude enzyme solution after recovering the microbial cells and disrupting or lysing the recovered cells. Furthermore, the aldolase or its fused protein may also be used after purifying by precipitation, filtration, column chromatography or other common technique as necessary. In this case, a purification method may also be used that uses an antibody of the aldolase or its fused protein.

When a protein inclusion body is formed, it is solubilized with a denaturant. Although it may be solubilized together with microbial cell protein, in consideration of the subsequent purification procedure, it is preferable to take out the inclusion body and then solubilize it. A method known in the prior art may be used to recover the inclusion body from the microbial cell. For example, the inclusion body may be recovered by disrupting the microbial cell followed by centrifugal separation. Examples of denaturants that solubilize protein inclusion bodies include guanidine hydrochloride (e.g., 6 M, pH 5-8) and urea (e.g., 8 M).

The protein inclusion body may be regenerated as active protein by removing these denaturants by treatment such as dialysis. Dialysis solutions such as Tris-HCl buffer or phosphate buffer may be used for dialysis, and the concentration may be from 20 mM to 0.5 M, and the pH may be from pH 5 to pH 8.

The protein concentration during the regeneration step is preferably held to about 500 μg/ml or less. In order to prevent the regenerated aldolase from undergoing self-crosslinking, the dialysis temperature is preferably 5° C. or lower. Furthermore, activity may also be expected to be restored by other methods used to remove denaturant such as dilution and ultrafiltration in addition to the aforementioned dialysis.

When the aldolase gene is derived from bacteria belonging to the genus *Pseudomonas*, the aldolase may be expressed and produced by using the *Pseudomonas* species bacteria as a host in one preferable mode. Descriptions of examples of host cells in this case include a report on a recombinant expression method in *Pseudomonas syringae* by Shi-En Lu et al. (FEMS Microbiology Letters 210 (2002) p. 115-121), a report on a recombinant expression method in *Pseudomonas aeruginosa* by Olsen, R. H. et al. (Journal of Bacteriology, (1982) 150, p. 60-69) and a report on a recombinant expression method in *Pseudomonas stutzeri* by Grapner, S. et al. (Biomol. Eng., (2000), 17, p. 11-16). However, the *Pseudomonas* species bacteria used as host cells for expressing aldolase are not limited to those recited herein.

Next, with respect to the vector used to introduce aldolase gene into *Pseudomonas* species bacteria, a plasmid may be used that has a replication starting point which function inside *Pseudomonas* species bacterial cells. For example, plasmid pKLH4.05 has been reported by Eza Kalyaeva et al. to have a replicon TFK that function in *Pseudomonas aeruginosa*. Wide-spectrum host vectors may also be used that are used to transform Gram-negative bacteria. These vectors are known to function in *Pseudomonas* species bacteria as well, examples of which include RK404 (Ditta, G et al., Plasmid 13 (1985) p. 149-153) and RSF1010 (Frey, J. et al., Gene 24 (1982) p. 289-296).

In the case of using the DNA indicated in SEQ ID No: 1 for the DNA that encodes aldolase, aldolase is produced that has the amino acid sequence of SEQ ID No: 2 or 3, and in the case of using the DNA indicated in SEQ ID No: 15, aldolase is produced that has the amino acid sequence of SEQ ID No: 16.

[II] Method for Producing Substituted α-Keto Acid Using Aldolase

Next, a description is provided of the method for producing substituted α-keto acid of the present invention. The method for producing substituted α-keto acid of the present invention is a method for producing the substituted α-keto acid represented by the following general formula (3):

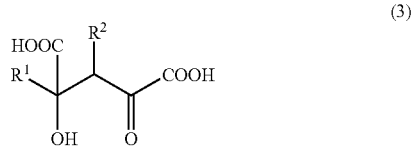

by reacting the substituted α-keto acid represented by the following general formula (1):

with the substituted α-keto acid represented by the following general formula (2):

wherein the reaction is performed in the presence of a protein that catalyzes the reaction.

In general formula (1), $R^1$ represents an alkyl group having 1 to 8 carbon atoms, an alkoxyl group having 1 to 8 carbon atoms, a carboxyalkyl group having 2 to 9 carbon atoms, an aryl or an aralkyl group having up to 20 carbon atoms, a heterocycle-containing hydrocarbon group having up to 11 carbon atoms, a hydroxyl group or an ester derivative thereof. $R^1$ may also be substituted with a halogen atom, a hydroxyl group, an alkyl group having up to 3 carbon atoms, an alkoxy group having up to 3 carbon atoms or an amino group. $R^1$ is preferably a substituent having 4 or more carbon atoms and preferably 6 or more carbon atoms, while an aryl group or an aralkyl group having up to 20 carbon atoms (aryl groups such as a phenyl group, a tolyl group, a xylyl group, a biphenyl group, a naphthyl group, an anthryl group or a phenantolyl group; an aralkyl groups such as a benzyl group, a benzhydryl group, a styryl group, a phenethyl group, a trityl group or a cinnamyl group), and a heterocycle-containing hydrocarbon group having up to 11 carbon atoms (heterocyclic groups such as a furyl group, a thienyl group, a pyridyl group, a piperidyl group, a piperidino group, a morpholino group or an indolyl group; alkyl groups substituted by these heterocyclic groups) are particularly preferable. $R^1$ is particularly preferably a benzyl group or a 3-indolylmethyl group, and a 3-indolylmethyl group is the most preferable. Namely, phenyl pyruvic acid or indole pyruvic acid is preferable for the substituted α-keto acid of general formula (1), and indole pyruvic acid is particularly preferable.

In general formula (2), $R^2$ represents an alkyl group having 1 to 8 carbon atoms, an alkoxyl group having 1 to 8 carbon atoms, a carboxyalkyl group having 2 to 9 carbon atoms, an aryl or an aralkyl group having up to 20 carbon atoms, a heterocycle-containing hydrocarbon group having up to 11 carbon atoms, a hydroxyl group or an ester derivative thereof. When $R^2$ contains an aromatic ring or a hetero ring, the aromatic ring or hetero ring may be substituted with at least one type of substituent selected from the group consisting of a halogen atom, a hydroxyl group, an alkyl group having up to 3 carbon atoms, an alkoxy group having up to 3 carbon atoms and an amino group. However, when $R^1$ represents a hydrogen atom, a methyl group or a carboxymethyl group in general formula (1), $R^2$ does not represent a hydrogen atom. $R^2$ is preferably a hydrogen atom or a carboxyl group, and particularly preferably a hydrogen atom. Namely, the substituted α-keto acid of general formula (2) is preferably oxalacetic acid or pyruvic acid, and particularly preferably pyruvic acid.

In general formula (3), $R^1$ and $R^2$ have the same meanings as $R^1$ and $R^2$ in general formulas (1) and (2).

In the production process of a substituted α-keto acid of the present invention, it is most preferable to synthesize IHOG shown in the following formula (4) by using indole pyruvic acid for the substituted α-keto acid of general formula (1), and using pyruvic acid for the substituted α-keto acid of general formula (2).

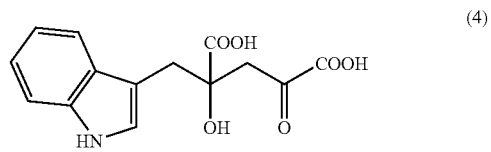

There are no particular limitations on the protein that catalyzes the reaction, and any protein may be used provided it is a protein that is capable of catalyzing a reaction that synthesizes the substituted α-keto acid represented by the general formula (3) by aldol condensation of the substituted α-keto acid represented by the general formula (1) and the substituted α-keto acid represented by the general formula (2).

Namely, as long as the protein catalyzes the reaction, it may be a protein derived from a microorganism or a protein synthesized by a chemical synthesis process.

A preferable example of such a protein is the aldolase explained in section [1] describing aldolase. In this case, aldolase may be used which has been obtained by cultivating microbial cells that form protein that catalyzes the reaction (aldolase) among microorganisms belonging to the genus *Pseudomonas*, *Erwinia*, *Flavobacterium*, or *Xanthomonas*, or (2) aldolase may be used which has been obtained by producing a transformant that forms a protein that catalyzes the reaction using recombinant DNA technology followed by cultivating the transformant.

The protein that catalyzes the reaction may be added in any form to the reaction mixture provided it is able to catalyze the reaction that synthesizes the aforementioned substituted α-keto acid represented by general formula (3). Namely, the protein that catalyzes the reaction may be added to the reaction mixture by itself, or it may be added to the reaction mixture in the form of a composition having aldolase activity that contains a protein that catalyzes the reaction (aldolase).

A "composition having aldolase activity" here is only required to be one which contains a protein that catalyzes the reaction (aldolase), and specific examples include a culture, medium (in which microbial cells have been removed from a culture), microbial cells (including both cultivated microbial cells and washed microbial cells), a treated microbial cell product that have been disrupted or lysed, and a composition having aldolase activity obtainable from purifying any of the medium and cells or both (crude enzyme solution, purified enzyme). For example, in the case of producing a substituted α-keto acid using aldolase-producing microorganisms or cells that have been transformed by a recombinant DNA, the substrate may be added directly to the culture while cultivating, or may be used in the form of microbial cells or washed microbial cells that have been separated from the culture. Furthermore, a treated microbial cell product that have been disrupted or lysed may be used directly, or the aldolase may be recovered from the treated microbial cell product and used as a crude enzyme solution, or used after purifying the enzyme. Namely, as long as it is in the form of a fraction that has aldolase activity, it may be used in the process for producing a substituted α-keto acid of the present invention in any form.

In order to perform an aldol reaction using aldolase or a composition having aldolase activity, a reaction solution containing a substituted α-keto acid represented by the general formula (1), a substituted α-keto acid represented by the general formula (2) and a protein or aldolase-containing composition that catalyzes the reaction is adjusted to a suitable temperature of 20 to 50° C. and allowing to stand undisturbed, shaking or stirring for 30 minutes to 5 days while maintaining at pH 6 to 12.

The reaction velocity may also be improved by adding a bivalent cation such as $Mg^{2+}$, $Mn^{2+}$, $Ni^{2+}$, or $Co^{2+}$ to the reaction mixture. $Mg^{2+}$ may be used preferably in terms of cost and so forth.

When adding these bivalent cations to the reaction solution, although any salt may be used provided it does not hinder the reaction, $MgCl_2$, $MgSO_4$, $MnSO_4$, and so forth may be used preferably. The concentrations of these bivalent cations may be determined by simple preliminary studies conducted by a person with ordinary skill in the art. These bivalent cations may be added within the range of 0.01 mM to 10 mM, preferably 0.1 mM to 5 mM, and more preferably 0.1 mM to 1 mM.

As a preferable example of reaction conditions when performing the process for producing substituted α-keto acid of the present invention, an enzyme source in the form of washed cells of aldolase-expressing *E. coli* are added at 10% (w/v) to a reaction solution consisting of 100 mM buffer, 50 mM indole-3-pyruvic acid, 250 mM pyruvic acid, 1 mM $MgCl_2$ and 1% (v/v) toluene followed by reacting while shaking at 33° C. for 4 hours to obtain 4-(indol-3-ylmethyl)-4-hydroxy-2-oxoglutarate (IHOG).

The substituted α-keto acid of general formula (3) that is formed may be separated and purified according to known techniques. Examples of the method may include a method in which the substituted α-keto acid is contacted with an ion exchange resin to adsorb basic amino acids followed by elution and crystallization, and a method in which the product obtained by elution is discolored and filtrated with activated charcoal followed by crystallization to obtain substituted α-keto acid.

Use of the process for producing substituted α-keto acid of the present invention makes it possible to form a precursor keto acid (IHOG) of monatin from indole pyruvic acid and oxalacetic acid (or pyruvic acid). Since IHOG may be used to derive monatin by aminating position 2, it is useful as an intermediate in monatin synthesis.

EXAMPLES

The present invention will be explained in further detail with reference to examples shown below, however, the invention is not limited thereto. In the examples, IHOG and PHOG used as substrates were synthesized according to the processes described in Reference Examples 1 and 2.

Example 1

[I] Screening of Microorganisms Having Aldolase Activity for PHOG

Microbial strains having aldolase activity using 4-phenylmethyl-4-hydroxy-2-oxoglutarate (PHOG) as a substrate were screened for.

Microorganisms (bacteria, yeast) were inoculated onto bouillon plate medium (Eiken Chemical Co., Ltd.) and cultivated at 30° C. for 24 hours. The microorganisms were then inoculated onto plates containing 0.5 g/dl glycerol, 0.5 g/dl fumaric acid, 0.3 g/dl yeast extract, 0.2 g/dl peptone, 0.3 g/dl ammonium sulfate, 0.3 g/dl $K_2HPO_4$, 0.1 g/dl $KH_2PO_4$, 0.05 g/dl $MgSO_4 \cdot 7H_2O$, 0.25 g/dl sodium phthalate and 2 g/dl agar powder (pH 6.5) followed by cultivating at 30° C. for 24 hours. The resulting microbial cells were inoculated into a reaction solution comprised of 100 mM Tris-HCl (pH 8.0), 50 mM PHOG, 1 mM $MgCl_2$, 5 mM potassium phosphate solution (KPi) and 1% (v/v) toluene to wet cells weight of about 1% (w/v), and incuvated at 30° C. for 24 hours. The concentration of free pyruvic acid in the reaction solution was quantified by an enzymatic method using lactate dehydrogenase (LDH). 10 µl of sample was then added to 200 µl of a reaction solution comprised of 100 mM Tris-HCl (pH 8.0), 1.5 mM NADH, 5 mM $MgCl_2$ and 25 U/ml LDH followed by incubating at 30° C. for 10 minutes. The optical absorbance at 340 nm was measured after the reaction, and the amount of pyruvic acid in the sample was quantified from the reduction in the amount of NADH.

The amount of phenyl pyruvic acid formed was quantified by HPLC analysis using an "Inertsil ODS-2" column (GL Sciences Inc., 5 µm, 4.6×250 mm). The analysis conditions were as indicated below.

Mobile phase: 20% (v/v) acetonitrile/0.05% (v/v) aqueous trifluoroacetic acid

Flow rate: 1 ml/min

Column temperature: 40° C.

Detection: UV210 nm

Under these conditions, PHOG was eluted at retention time of about 9.8 minutes while phenyl pyruvic acid was eluted at a retention time of about 12 minutes, and each was able to be separated and quantified.

The value obtained by subtracting the amount of pyruvic acid or phenyl pyruvic acid formed from PHOG in a reference (microorganism non-addition reaction) from the amount formed in a test microorganism addition reaction was used to indicate the amount formed by aldolase. As a result, aldolase activity using PHOG as substrate was found for the microbial strains listed in Table 1.

TABLE 1

Results of Screening for Microbial Strains Having Aldolase Activity for PHOG

| Microbial strain | Pyruvic acid (mM) | Phenylpyruvic acid (mM) |
| --- | --- | --- |
| Pseudomonas taetrolens ATCC4683 | 34.9 | 35.0 |
| Pseudomonas coronafaciens AJ2791 | 33.6 | 33.9 |
| Pseudomonas desmolytica AJ1582 | 1.1 | 2.9 |
| Erwinia sp. AJ2917 | 0.8 | 3.0 |
| Flavobacterium rhenanum CCM298 AJ2468 | 3.0 | 6.1 |
| Xanthomonas citri AJ2797 | 1.0 | 3.2 |

PHOG was synthesized from phenyl pyruvic acid and oxalacetic acid or pyruvic acid using *Pseudomonas taetrolens* ATCC4683 cells. Microbial cells of *P. taetrolens* ATCC4683 (AJ2212) were inoculated to a final concentration of about 1% (w/v) into a reaction solution comprised of 100 mM Tris-HCl (pH 8.0), 50 mM phenyl pyruvic acid, 1 mM $MgCl_2$, 5 mM KPi, 100 mM oxalacetic acid, or pyruvic acid and 1% (w/w) toluene, followed by incuvation at 30° C. for 16 hours. After the reaction, the amount of PHOG formed was quantified by HPLC. The amounts of PHOG formed from phenyl pyruvic acid and oxalacetic acid or pyruvic acid are shown in Table 2.

TABLE 2

Amounts of PHOG Formed from Phenyl Pyruvic Acid and Oxaloacetic Acid and/or Pyruvic Acid

| | Oxaloacetic acid lot | Pyruvic acid lot |
| --- | --- | --- |
| Microorganism addition lot | 14.3 (mM) | 9.3 (mM) |
| Control (Mg addition) lot | 8.6 | 1.7 |
| Control (Mg non-addition) lot | trace | N.D. |

According to Table 2, an increase in the amount of PHOG formed was observed in the microorganism addition reaction, and PHOG was determined to be able to be formed by the action of aldolase for both the combinations of phenyl pyruvic acid+oxalacetic acid and phenyl pyruvic acid+pyruvic acid.

[II] Purification of IHOG-Aldolase Derived from *Pseudomonas taetrolens* Strain ATCC4683

IHOG-aldolase was purified as described below from a soluble fraction of *P. taetrolens* strain ATCC4683. Aldolase activity using PHOG as a substrate was measured under the following conditions.

Reaction conditions: 50 mM Tris-HCl (pH 8.0), 2 mM PHOG, 0.2 mM NADH, 0.2 mM KPi, 1 mM $MgCl_2$, 16 U/ml of lactate dehydrogenase and 3 μL enzyme/600 μl reaction solution, optical absorbance at 340 nm measured at 30° C.

(1) Preparation of Soluble Fraction

A loopful of *P. taetrolens* ATCC4683 cells cultivated at 30° C. for 24 hours on bouillon plate medium was picked from the plate, and inoculated into a 500 ml volumetric flask containing 50 ml of enzyme production medium (0.5 g/dl glycerol, 0.5 g/dl fumaric acid, 0.5 g/dl ammonium sulfate, 0.3 g/dl $K_2HPO_4$, 0.1 g/dl $KH_2PO_4$, 0.05 g/dl $MgSO_4 \cdot 7H_2O$, 0.3 g/dl yeast extract, 0.2 g/dl peptone, 0.25 g/dl sodium phthalate and 0.005% Antifoam A (Sigma), adjusted to pH 6.5 with KOH) followed by shaken-culturing at 30° C. for 24 hours. 0.5 ml of the culture was inoculated into 500 ml volumetric flasks containing 50 ml of enzyme production medium followed by shake culture at 30° C. for 24 hours. The microorganisms were collected from the resulting culture (total 2 L) by centrifugation, and after washing by suspending in buffer A (20 mM Tris-HCl (pH 7.6)), were again recovered by centrifugation. The resulting washed microbial cells were suspended in 200 ml of buffer A and then ultrasonically disrupted at 4° C. for 30 minutes. The microbial cell residue was removed from the disruption solution by centrifugation (x8000 rpm, 10 min×2 times) followed by additional ultracentrifugation (x50000 rpm, 30 min). After the ultracentrifugation, the resulting supernatant was obtained as the soluble fraction.

(2) Anionic Exchange Chromatography: Q-Sepharose FF 80 ml of the aforementioned soluble fraction was applied to an anionic exchange chromatography column, Q-Sepharose FF 26/10 (Pharmacia, CV=20 ml) equilibrated with buffer A, and adsorbed onto the carrier. After washing out any unbound proteins using buffer A, the adsorbed protein was eluted using liner gradient of the KCl concentration from 0 M to 0.7 M (total: 140 ml). aldolase activity for PHOG was detected in the fraction equivalent to about 0.5 M. The same chromatography procedure was repeated twice.

(3) Hydrophobic Chromatography: Phenyl Sepharose HP HR 16/10

The fraction in which aldolase activity had been detected was dialyzed at 4° C. overnight against buffer B (50 mM Tris-HCl (pH 7.6), 1 M ammonium sulfate, pH 7.6) and then filtered with a 0.45 μm filter. The resulting filtrate was applied to a hydrophobic chromatography column, Phenyl Sepharose HP HR 16/10 (Pharmacia) equilibrated with buffer B. The aldolase was adsorbed to the carrier.

After washing out any unbound proteins using buffer B, aldolase was eluted using liner gradient of the ammonium sulfate concentration from 1 M to 0 M. The aldolase activity was detected in the elution fraction where the concentration of ammonium sulfate was about 0.2M.

(4) Gel Filtration Chromatography: Sephadex 200 HP 16/60

Each fraction containing aldolase was collected, dialyzed against buffer A and filtered with a 0.45 μm filter. The resulting filtrate was concentrated using the Centriprep 10 ultrafiltration membrane. The resulting concentrate was applied to a gel filtration chromatography column, Sephadex 200 HP 16/60 (Pharmacia) equilibrated with buffer C (20 mM Tris-HCl (pH 7.6), 0.1 M KCl), and eluted at a flow rate of 1 ml/min. the aldolase was eluted in the fraction from 66 to 71 ml. The molecular weight of the aldolase as determined from the elution position of peak activity was estimated to be about 146 kDa.

(5) Anionic Exchange Chromatography: Mono Q HR5/5

The resulting fraction was filtered with a 0.45 μm filter. Here, the resulting filtrate was applied to an anionic exchange chromatography column, Mono Q HR 5/5 (Pharmacia)

equilibrated with buffer A. The aldolase was adsorbed to the carrier. After washing out any unbound proteins with buffer A, protein was eluted using liner gradient of the KCl concentration from 0 mM to 700 mM (total: 24 ml). The aldolase activity was measured for each eluted fraction, and aldolase activity was observed at the elution position where the KCl concentration was about 0.4 M.

(6) Hydroxyapatite Chromatography: CHT-II

The resulting fraction was dialyzed at 4° C. overnight against buffer D (10 mM potassium phosphate buffer (pH 7.0)), and filtered with a 0.45 μm filter. Here, the resulting filtrate was applied to a hydroxyapatite chromatography column, 5 ml CHT-II (BioRad) equilibrated with buffer D. The aldolase activity was detected at the unbound fraction, aldolase was able to be separated from the adsorbed protein.

When the fraction purified according to the column chromatography procedures described above was applied to SDS-PAGE, a nearly single band was detected at the location corresponding to about 25 kDa. Since the estimated molecular weight as determined by gel filtration chromatography was about 146 kDa, it was suggested that the aldolase forms a hexamer. The purification table is shown in Table 3.

TABLE 3

Purification Table of IHOG Aldolase Derived from *Pseudomonas taetrolens* Strain ATCC4683

|  | protein (mg) | specific activity (U/mg) | purification fold | total activity (U) | yield (%) |
| --- | --- | --- | --- | --- | --- |
| soluble fraction | 3750 | 0.014 | 1 | 51 | 100 |
| Q-sepharose HP 26/10 | 510 | 0.060 | 4.4 | 30.5 | 59.8 |
| Phenyl sepharose HP 16/10 | 21.2 | 0.893 | 66 | 19.0 | 37.2 |
| Sephadex200 HP 16/60 | 1.9 | 4.643 | 341 | 8.65 | 17.0 |
| monoQ HR5/5 | 0.49 | 10.89 | 800 | 5.33 | 10.4 |
| Hydroxyapatite CHT-II | 0.025 | 28.70 | 2110 | 0.71 | 1.4 |

[III] Determination of Internal Amino Acid Sequence of IHOG Aldolase

After applying an approximately 2 μg aliquot of the purified aldolase to SDS-PAGE, the sample in the SDS-PAGE gel was treated with trypsin (pH 8.5, 35° C., 20 hours) and then applied to reverse phase HPLC to separate the fragment peptides. Amino acid sequences consisting of 20 residues and 12 residues, respectively (SEQ ID Nos: 4 and 5), were determined as shown below for two of the separated fractions.

TABLE 4

Determined Internal Amino Acid Sequences

| SEQ ID No. 4 | SLLDAFQNVV TPHIS DNLGR |
| --- | --- |
| SEQ ID No. 5 | AEIAT GALDQ SW |

[IV] Cloning of IHOG-Aldolase Gene Derived from *P. taetrolens* Strain ATCC4683

(1) Preparation of Chromosomal DNA

*P. taetrolens* strain ATCC4683 was cultivated at 30° C. overnight with 50 ml of bouillon medium (pre-cultivation). 5 ml of this culture was inoculated into the 50 ml of fresh bouillon medium. After the cultivation until the late logarithmic growth phase, 50 ml of culture was centrifuged (12000 xg, 4° C., 15 minutes) to recover the microorganisms. A chromosomal DNA was then prepared according to established methods using these microbial cells.

(2) Cloning of a Internal DNA of the Aldolase Gene by PCR

The following mixed primers (SEQ ID Nos: 6 and 7) were synthesized based on the internal amino acid sequence determined for IHOG-aldolase.

TABLE 5

Mixprimers Designed and Synthesized Based on Internal Amino Acid Sequence

| SEQ ID No. 6 | TTY CAR AAY GTS GTS ACS CCS C |
| --- | --- |
| SEQ ID No. 7 | TGR TCR ATN GCN CCS GTN GCR ATY TCN GC |

Amplification was performed by PCR with the synthesized mixed primers and the chromosomal DNA of *P. taetrolens* ATCC4683 as a template. The PCR reaction was performed with the PCR Thermal PERSONEL (Takara) for 30 cycles under the conditions indicated below.

94° C., 30 seconds
55° C., 30 seconds
72° C., 1 minute

The PCR product was applied to agarose gel electrophoresis, and an approximately 500 bp fragment was amplified. This DNA fragment was cloned to pUC18, followed by determination of the nucleotide sequence. The amino acid sequence estimated from the obtained DNA fragment matched with the internal amino acid sequence of IHOG aldolase, thereby confirming that the desired aldolase gene had been obtained.

(3) Cloning of the Full Length Gene by Colony Hybridization

The full-length gene was cloned by Southern hybridization analysis and colony hybridization with the DNA fragment amplified by PCR. The DNA probe was produced by using DIG High Prime (Roche Diagnostics K.K.), incubating overnight (i.e., O/N) at 37° C. according to the instruction manual to label the probe. Southern hybridization analysis was performed according to the manual by digesting 1 μg of chromosomal DNA with each of restriction enzyme, electrophoresing in 0.8% agarose gel and blotting onto a nylon membrane. Hybridization was performed using DIG Easy Hyb (Roche Diagnostics K.K.) by pre-hybridizing at 50° C. for 1 hour, adding the probe and then hybridizing with O/N. Bands were detected using the DIG Nucleotide Detection Kit. As a result, an approximately 4 kbp PstI fragment was detected that strongly hybridized by using the PCR fragment as a probe. Next, this PstI fragment was obtained by colony hybridization. 20 μg of chromosomal DNA was treated with PstI followed by applying to agarose gel electrophoresis and recovering a fragment of which size was about 4 kbp. This was then ligated into pUC118 to produce a library in *E. coli* JM109. The colonies were then transferred to a nylon membrane filter (Hybond-N, Amersham) followed by alkaline denaturation, neutralization and immobilization treatment. Hybridization was performed using DIG Easy Hyb. The filter was immersed in a buffer and pre-hybridized at 42° C. for 1 hour. Subsequently, the previously prepared labeled probe was added, followed by hybridization at 42° C. for 16 hours. After washing with SSC, colonies that hybridized with the probe were detected using the DIG Nucleotide Detection Kit (Roche Diagnostics K.K.). As a result, a clone was obtained that strongly hybridized with the probe.

The nucleotide sequence of plasmid DNA recovered from the obtained clone was determined, and it was clearly demonstrated to have the nucleotide sequence of SEQ ID No: 1. An orf of 678 bp that contained the nucleotide sequence corresponding to the determined amino acid sequence (numbers 507 to 566 and numbers 1046 to 1082 in SEQ ID No: 1) was found and the entire length of the desired aldolase gene was obtained.

(4) Expression of IHOG-Aldolase in *E. coli* (Part 1)

The fragment amplified using the primers shown in Table 6 (SEQ ID Nos: 8 and 9) from a chromosomal DNA of *P. taetrolens* ATCC4683 was digested with BamHI/HindIII, inserted into the BamHI/HindIII site of pUC18, to construct plasmid pUCALD. *E. coli* JM109 was transformed with thus obtained pUCALD, and the transformant was cultured at 37° C. overnight in LB medium containing 50 µg/ml of ampicillin (pre-cultivation). The pre-culture was inoculated at 1% in 50 ml of LB medium followed by cultivating at 37° C. IPTG was added to a final concentration of 1 mM at about 2 hours after the start of cultivating, followed by additionally cultivating for 3 hours. After cultivating, the microorganisms were recovered, washed, and then suspended in 1 ml of 20 mM Tris-HCl (pH 7.6) followed by disrupting the microbial cells using a Multi-Beads Shocker (Yasui Kikai Corporation). The crude extract was then centrifuged at 15000 rpm for 10 minutes, and the resulting supernatant was used as a crude enzyme solution.

TABLE 6

Primer

SEQ ID No. 8 ALD-5'Bam(5'-GCC GGA TCC ACA AGG GTT CAG TCA TTC ATG G-3')

SEQ ID No. 9 ALD-3'Hind(5'-CCG AAG CTT TCA GTT CGC CAG GCC AGC C-3')

When aldolase activity was measured using the crude enzyme solution and PHOG as a substrate, in contrast to aldolase activity for PHOG not being detected in the *E. coli* harboring pUC18 (control), aldolase activity for PHOG of 0.81 U/mg protein was detected in the strain harboring pUCADL. As a result, the gene was demonstrated to encode the desired aldolase.

[V] Synthesis of 4-(indol-3-ylmethyl)-4-hydroxy-2-oxoglutarate (IHOG) from Indole-3-Pyruvic Acid and Pyruvic Acid Using an Aldolase-Expressing Strain 4-(indol-3-ylmethyl)-4-hydroxy-2-oxoglutarate (IHOG) was synthesized from indole-3-pyruvic acid and pyruvic acid with washed cells of the aldolase-expressing *E. coli* produced in [IV] as the enzyme source. The amount of IHOG was determined by HPLC analysis using the "Inertsil ODS-2" (GL Sciences Inc., 5 µm, 4.6×250 mm). The analysis conditions are as indicated below.

Mobile phase: 40% (v/v) acetonitrile/5 mM tetrabutyl ammonium dihydrogen phosphate solution
Flow rate: 1 ml/min
Column temperature: 40° C.
Detection: UV 210 nm Washed cells of aldolase-expressing *E. coli* were added at 10% (w/v) to a reaction solution comprised of 100 mM buffer (Tris-HCl 8.0, 9.0, or glycine-NaOH 10.0) 50 mM indole-3-pyruvic acid, 250 mM pyruvic acid, 1 mM $MgCl_2$ and 1% (v/v) toluene, and allowed to react by shaking at 33° C. for 4 hours. The enzyme reaction solution was suitably diluted and the amount of IHOG formed was quantified.

TABLE 7

Amount of IHOG Formed by Aldolase

| pH | aldolase | IHOG (mM) |
|---|---|---|
| 8 | + | 9.2 |
| 8 | − | 0.42 |
| 9 | + | 12.1 |
| 9 | − | 1.6 |
| 10 | + | 10.7 |
| 10 | − | 5.4 |

As a result, the amount of IHOG produced increased in the aldolase-expressing *E. coli* addition group, and IHOG was formed by the aldolase.

Example 2

High-Level Expression of IHOG-Aldolase in *E. coli* (Part 2)

(1) Construction of Plasmid pTrp4 Containing trp Promoter and rrnB Terminator

The promoter region of the trp operon in a chromosomal DNA of *E. coli* W3310 by PCR with the oligonucleotides shown in Table 8 as primers (combination of SEQ ID No: 10 and 11), and the resulting DNA fragment was ligated into a pGEM-Teasy vector (Promega). *E. coli* JM109 was then transformed with this ligation mixture, and a strain was selected among ampicillin-resistant strains that had the desired plasmid in which the trp promoter was inserted in the opposite orientation of the lac promoter. Next, the DNA fragment containing trp promoter obtained by treating this plasmid with Eco0109I/EcoRI was ligated with the product of treating pUC19 (Takara) with Eco0109I/EcoRI. *E. coli* JM109 was then transformed with this ligation mixture, a strain was selected among ampicillin-resistant strains that had the desired plasmid, and that plasmid was named ptrp1. Next, pKK223-3 (Amersham-Pharmacia) was treated with HindIII/HincII, and the resulting DNA fragment containing rrnB terminator was ligated with the product of treating pTrp1 with HindIII/PvuII. *E. coli* JM109 was then transformed with this ligation mixture, a strain was selected among ampicillin-resistant strains that had the desired plasmid, and that plasmid was named pTrp2. Next, the trp promoter region was amplified by PCR with pTrp2 as a template and the oligonucleotides shown in the table as primers (combination of SEQ ID Nos: 10 and 12). This DNA fragment was treated with Eco0109I/NdeI and ligated with the product of treating pTrp2 with Eco0109I/NdeI. *E. coli* was then transformed with this ligation mixture, a strain was selected among ampicillin-resistant strains that had the desired plasmid, and that plasmid was named pTrp4.

TABLE 8

Primer

SEQ ID No. 10 5'-side  GTATCACG<u>AGGCCCT</u>AGCTGTGGTGTCATGGTCGGTGATC
                              Eco0109

SEQ ID No. 11 3'-side  TTCGGGGATTC<u>CATATG</u>ATACCCTTTTTACGTGAACTTGC
                                  NdeI SEQ ID No. 12 3'-side  GGGGGGGG<u>CATATG</u>CGACCTCCTTATTACGTGAACTTG
                                NdeI (2) Construction of Aldolase Gene-Expressing Plasmids ptrpALD1 and ptrpALD2, and Expression in *E. coli*

A fragment amplified from a chromosomal DNA of *P. taetrolens* ATCC4683 using the primers shown in Table 9 (SEQ ID Nos: 9 and 13) was digested with NdeI/HindIII to construct plasmid ptrpALD1 inserted into the NdeI/HindIII site of pTrp4. This plasmid expresses aldolase gene composing the amino acid sequence of SEQ ID No: 3 translated from the 444th ATG in the nucleotide sequence of SEQ ID No: 1 as the initiation codon. Furthermore, a fragment amplified from a chromosomal DNA of *P. taetrolens* ATCC4683 with primers (SEQ ID Nos: 9 and 14) was digested with NdeI/HindIII to construct plasmid ptrpALD2 inserted into the NdeI/HindIII site of pTrp4. This plasmid expresses aldolase gene composing the amino acid sequence of SEQ ID No: 2 translated from the 456th ATG in the nucleotide sequence of SEQ ID No: 1 as the initiation codon. Each of the constructed expression plasmids was introduced into *E. coli* JM109, and the transformants were cultured at 37° C. overnight in LB medium containing 50 µg/ml of ampicillin (pre-cultivation). The pre-culture was inoculated at 1% in 50 ml of LB medium followed by cultivation at 37° C. The microbial cells were harvested, washed and suspended in 1 ml of 20 mM Tris-HCl (pH 7.6) followed by disrupting the microbial cells using a Multi-Beads Shocker (Yasui Kikai Corporation). The crude extract was then centrifuged at 15000 rpm for 10 minutes and the resulting supernatant was used as a crude enzyme solution.

ml of this culture was inoculated into 50 ml of bouillon medium. After the cultivation until the late logarithmic growth phase, 50 ml of culture was centrifuged (12000×g, 4° C., 15 minutes) to recover the microorganisms. A chromosomal DNA was then prepared according to established methods using these microbial cells.

(2) Cloning of Full Length Gene by Southern Analysis and Colony Hybridization

Cloning of IHOG-aldolase gene derived from *P. coronafaciens* strain AJ2791 (hereinafter, "

treatment. Hybridization was performed using DIG Easy Hyb. The Nylon membrane filter was immersed in a buffer and pre-hybridized at 37° C. for 1 hour. Subsequently, the previously prepared labeled probe was added and hybridized at 37° C. for 16 hours. The Nylon membrane filter was washed twice at room temperature for 5 minute using 2×SSC and then washed twice at 37° C. for 15 minutes using 0.1× SSC. Colonies that hybridized with the probe were detected using the DIG Nucleotide Detection Kit (Roche Diagnostics K.K.). As a result, a clone was obtained that hybridized with the probe.

When the nucleotide sequence of plasmid DNA recovered from the positive clone was determined, a 744 bp orf was found, and the full length of the desired aldolase was obtained. The constructed plasmid inserted with the PcALD gene was named pUCPcALD.

E. coli JM109 was transformed with pUCPcALD, and the transformant was cultured at 37° C. for overnight in LB medium containing 50 µg/ml of ampicillin (LB-amp medium) (pre-cultivation). Thus obtained preculture was inoculated at 1% in 50 ml of fresh LBmedium, followed by cultivation at 37° C. IPTG was added to a final concentration of 1 mM at about 2 hours after the start of cultivating followed by additionally cultivating for 3 hours. After cultivating, the microorganisms were recovered, washed, and then suspended in 1 ml of 20 mM Tris-HCl (pH 7.6) followed by disrupting the microbial cells with a Multi-Beads Shocker (Yasui Kikai Corporation). The crude extract was then centrifuged at 15000 rpm for 10 minutes, and the resulting supernatant was used as a crude enzyme.

When aldolase activity was measured using the crude enzyme and PHOG as a substrate, in contrast to aldolase activity for PHOG not being detected in the E. coli harboring pUC18 (control), PHOG-aldolase activity of 39.3 U/mg protein was detected in the strain harboring pUCADL. As a result, the gene was demonstrated to encode the desired aldolase.

Example 4

Purification of Recombinant Enzyme of Aldolase Derived from Pseudomonas taetrolens Strain ATCC4683

Recombinant aldolase derived from P. taetrolens ATCC4683 (PtALD) was purified as described below from the soluble fraction of E. coli that highly expresses PtALD. Aldolase activity was determined by measuring aldolase activity when using PHOG as a substrate under the following conditions.
Reaction conditions: 50 mM Tris-HCl (pH 8.0), 2 mM PHOG 0.2 mM NAD, 0.2 mM KPi, 1 mM MgCl$_2$, 16 U/ml of lactate dehydrogenase and 3 µL enzyme/600 µl reaction mixture, optical absorbance at 340 nm measured at 30° C.
(1) Preparation of Soluble Fraction A loopful of E. coli JM109/ptrpALD2 cultured at 37° C. for 16 hours on LB-amp plate medium were picked from the plate, inoculated into a test tube containing 3 ml of LB-amp medium and shake-culture was performed at 37° C. for 16 hours. 0.5 ml of this culture was then inoculated into ten 500 ml volumetric flasks containing 50 ml of LB-amp medium followed by culturing at 37° C. for 16 hours. The microorganisms were recovered from the resulting culture by centrifugation, and after washing by suspending in buffer A (20 mM Hepes-KOH (pH 7.6)), were again recovered by centrifugation. The resulting washed microbial cells were suspended in 25 ml of buffer A and then ultrasonically disrupted at 4° C. for 30 minutes. The microbial cell residue was removed from the crude extract by centrifugation (x8000 rpm, 10 min×2 times) after which the resulting supernatant was used as the crude fraction.
(2) Anionic Exchange Chromatography: Q-Sepharose FF 23 ml of the crude fraction was applied to a Q-Sepharose FF 26/10 anionic exchange chromatography column (Pharmacia, CV=20 ml) equilibrated with buffer A and adsorbed onto the carrier. After washing out any unbound proteins using buffer A, the PtALD was eluted while linearly changing the KCl concentration from 0 M to 0.7 M (total: 140 ml). The aldolase activity for PHOG was observed in the fraction equivalent to about 0.5 M.
(3) Hydrophobic Chromatography: Phenyl Sepharose HP HR 16/10

The fraction detected aldolase activity was dialyzed at 4° C. overnight against buffer B (20 mM Hepes-KOH (pH 7.6), 1 M ammonium sulfate, pH 7.6) and then filtering the supernatant obtained with a 0.45 µm filter. The resulting filtrate was applied to a hydrophobic chromatography column, Phenyl Sepharose HP HR 16/10 (Pharmacia) equilibrated with buffer B. This procedure resulted in the aldolase being adsorbed to the carrier.

After washing out any unbound proteins using buffer B, aldolase was eluted using liner gradient of the ammonium sulfate concentration from 1 M to 0 M. The aldolase activity was detected at the elution position where the concentration of ammonium sulfate was about 0.2 M.

When the fraction purified according to the chromatography procedures described above was applied to SDS-PAGE, a single band was observed at the location corresponding to about 25 kDa with CBB staining. The resulting recombinant PtALD solution was dialyzed at 4° C. overnight against buffer A. As a result of the procedure, 17 ml of 350 U/ml PtALD solution was obtained.

Example 5

Purification of Recombinant Enzyme of Aldolase Derived from Pseudomonas coronafaciens Strain AJ2791

Recombinant aldolase derived from P. coronafaciens AJ2791 (PcALD) was purified from the soluble fraction of E. coli that highly expresses PcALD.

A loopful of E. coli JM109/pUCPcALD cells cultivated at 37° C. for 16 hours on LB-amp plate medium was picked from the plate, inoculated into a test tube containing 3 ml of LB-amp medium and shake-culture was performed at 37° C. for 16 hours. 0.5 ml of this culture was then inoculated into seven pieces of 500 ml volumetric flasks containing 50 ml of LB-amp medium (+0.1 mM IPTG) followed by shake-culturing at 37° C. for 16 hours. The microorganisms were recovered from the resulting culture by centrifugation, and after washing by suspending in buffer A (20 mM Hepes-KOH (pH 7.6)), were again recovered by centrifugation. The resulting washed microbial cells were suspended in 30 ml of buffer A and then ultrasonically disrupted at 4° C. for 30 minutes. The microbial cell residue was removed from the crude extract by centrifugation (x8000 rpm, 10 min×2 times) after which the resulting supernatant was used as the crude extraction fraction.

The resulting crude extraction fraction was purified by chromatography using the same procedure as the purification of recombinant PtALD described in Example 4. When a fraction purified by a two-stage chromatography procedure using Q-Sepharose and Phenyl Superose was applied to SDS- PAGE, a single band was observed at the location corresponding to about 25 kDa with CBB staining. The resulting recombinant PcALD solution was dialyzed at 4° C. overnight against buffer A. As a result of the aforementioned procedure, 10 ml of 108 U/ml PcALD solution was obtained.

Example 6

Synthesis of 4-(indol-3-ylmethyl)-4-hydroxy-2-oxoglutarate from Indole-3-Pyruvic Acid and Pyruvic Acid Using PtALD and PcALD 4-(Indol-3-ylmethyl)-4-hydroxy-2-oxoglutarate (IHOG) was synthesized from indole-3-pyruvic acid and pyruvic acid using the PtALD and PcALD produced in Examples 4 and 5 as enzyme sources. The amount of IHOG was determined by HPLC analysis using the "Inertsil ODS-2" (GL Sciences Inc., 5 μm, 4.6×250 mm). The analysis conditions are as indicated below.
Mobile phase: 40% (v/v) acetonitrile/5 mM tetrabutyl ammonium dihydrogen phosphate solution
Flow rate: 1 ml/min
Column temperature: 40° C.
Detection: UV210 nm
PtALD and PcALD were added at 1.8 U/ml and 0.8 U/ml, respectively, to a reaction solution comprised of 100 mM Hepes-KOH (pH 8.5), 50 mM indole-3-pyruvic acid, 250 mM pyruvic acid and 1 mM to 5 mM $MgCl_2$, and allowed to react at 33° C. for 4 hours. The enzyme reaction solution was suitably diluted and the amount of IHOG formed was quantified. As a result, IHOG was able to be formed from the aldolases.

TABLE 10

|  | $MgCl_2$ (mM) | IHOG (mM) |
|---|---|---|
| PcALD | 1 | 4.9 |
|  | 5 | 5.4 |
| PtALD | 1 | 11.4 |
|  | 5 | 10.5 |

Example 7

Enzymatic Synthesis of Various Substituted α-Keto Acids Using PtALD

The aldol condensation activity of pyruvic acid was measured for the various substrates shown in Table 11 using the PtALD produced in Example 4. A reaction solution was prepared composed of 100 mM glycine-NaOH (pH 9), 50 mM substrate, 250 mM sodium pyruvate, 1 mM $MgCl_2$ and 0.1 mg/ml PtALD, and incubated at 33° C. for 2 hours. The resulting reaction solution was subjected to ultrafiltration with an ultrafiltration membrane, Microcon 10 (Amicon) for a fraction molecular weight of 10000. 2 μl of the filtrate was diluted in 200 μl of 50% acetonitrile/0.1% aqueous ammonia solution followed by ESI-MS analysis.

As a result, peaks in the corresponding m/z values were detected for the substrates shown in Table 12, thus indicating that the desired pyruvic acid aldol condensates were formed.

TABLE 11

Aldol Condensates of Pyruvic Acid for Various Substrates Using PtALD

| Substrate | Substrate | Aldol Condensate | Exact MS (calculated) | [M-H]⁻ (measured) |
|---|---|---|---|---|
| indol-3-pyruvic acid |  |  | 291.1 | 290.2 |
| β-hydroxypyruvic acid |  |  | 192.03 | 191.19 |
| 2-ketobutyric acid |  |  | 190.05 | 189.19 |
| 3-methyl-2-oxobutanoic acid |  |  | 204.06 | 203.08 |

TABLE 11-continued

Aldol Condensates of Pyruvic Acid for Various Substrates Using PtALD

| Substrate | Substrate | Aldol Condensate | Exact MS (calculated) | [M-H]⁻ (measured) |
|---|---|---|---|---|
| α-ketoglutarate | | | 234.04 | 233.45 |
| pyruvic acid | | | 176.03 | 175.2 |
| D-arabinose | | | 238.07 | 237.15 |
| L-mannose | | | 268.08 | 267.72 |

TABLE 12

Aldol Condensates of Pyruvic Acid for Various Substrates Using PtALD

| Substrate | Substrate | Aldol Condensate | Exact MS (calculated) | [M-H]⁻ (measured) |
|---|---|---|---|---|
| L-ribose | | | 238.07 | 237.05 |

TABLE 12-continued

Aldol Condensates of Pyruvic Acid for Various Substrates Using PtALD

| Substrate | Substrate | Aldol Condensate | Exact MS (calculated) | [M-H]⁻ (measured) |
|---|---|---|---|---|
| N-acetyl-L-mannosamine | (structure) | (structure) | 309.27 | 308.48 |

Example 8

Enzymatic Properties of PtALD

A study was conducted on the following parameters regarding the PtALD prepared in Example 4.

Basic reaction conditions: 50 mM Hepes-KOH (pH 8.0), 2 mM PHOG, 5 mM MgCl$_2$, 3 mM KPB (pH 8), 16 U/ml of lactate dehydrogenase, measure a optical absorbance at 340 nm measured at 30° C.

(1) Kinetics Constants When Using PHOG as Substrate

Figure 2:
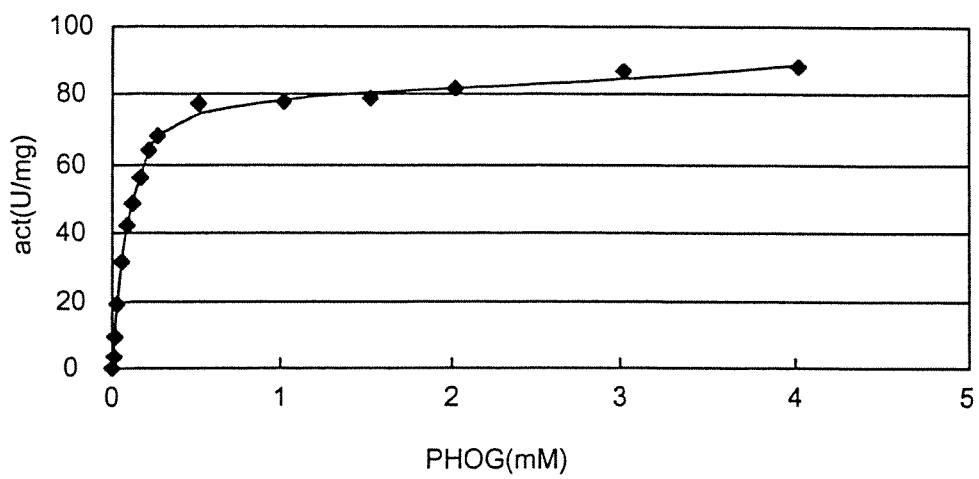
FIG. 2 shows the results of measuring the aldolase activity of aldolase derived from *Pseudomonas taetrolens* ATCC4683 (PtALD) versus PHOG concentration.
Figure 3:
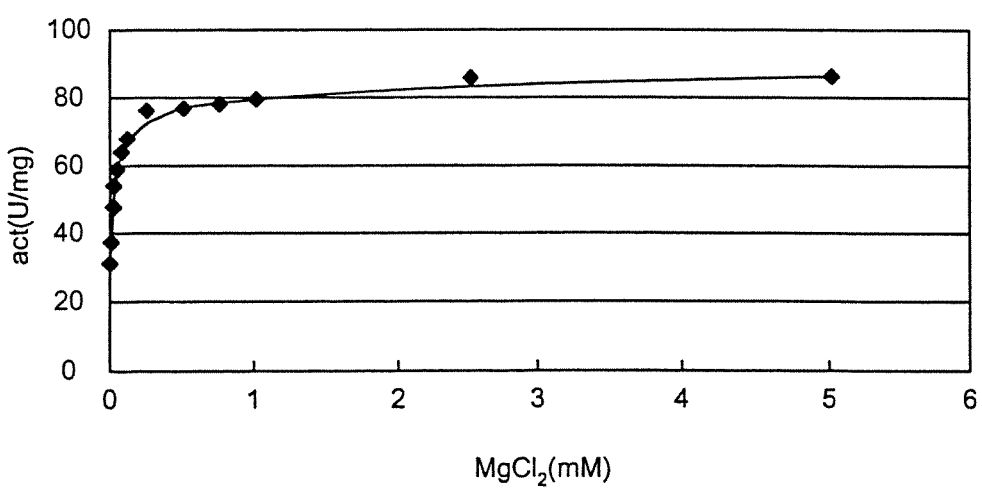
FIG. 3 shows the results of measuring the aldolase activity of PtALD versus MgCl₂ concentration.
Figure 4:
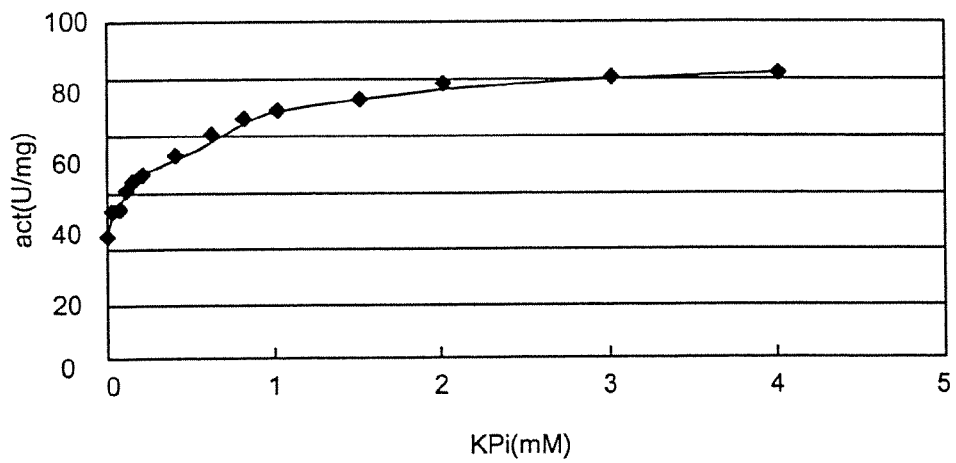
FIG. 4 shows the results of measuring the aldolase activity of PtALD versus KPi concentration.

Vmax (for PHOG)=91.7 μmol/min/mg, Km (for PHOG)=0.10 mM, Km (for MgCl$_2$)=0.019 mM, and Ka (for KPi)=0.95 mM were respectively determined from the results shown in FIGS. 2 to 4. The aldolase activity increased by 2.7 times as compared with a non-addition lot following addition of 1 mM MgCl$_2$, and increased 2 times as compared with a non-addition lot following addition of 5 mM KPB.

Figure 5:
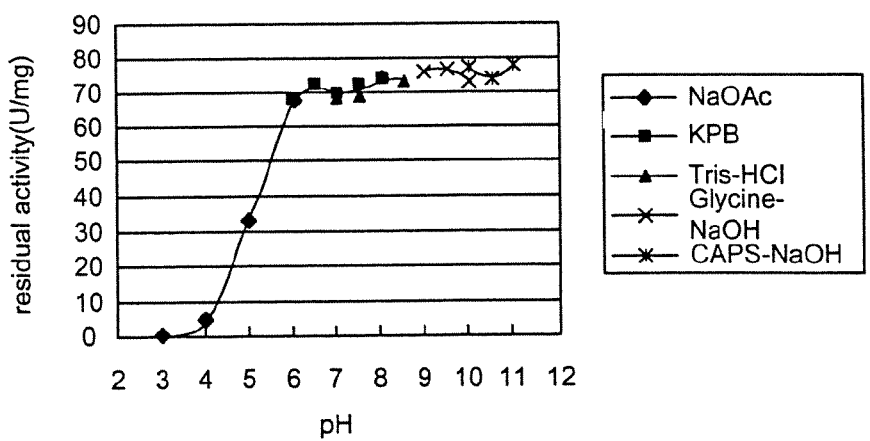
FIG. 5 shows the results of measuring the pH stability of PtALD.

(2) pH Stability pH stability was measured over a range of pH 3 to pH 11. The buffers used for measurement were as follows: sodium acetate buffer (pH 3, 4, 5, 6), potassium phosphate buffer (pH 6, 6.5, 7, 7.5), Tris-HCl buffer (pH 7, 7.5, 8, 8.5), glycine-NaOH buffer (pH 9, 9.5, 10), CAPS-NaOH buffer (pH 10, 10.5, 11). The residual activity after incubating PtALD at 37° C. for 30 minutes in each of the buffer solutions at a concentration of 100 mM was measured under the basic reaction conditions. Those results are shown in FIG. 5.

(3) Temperature Stability

Figure 6:
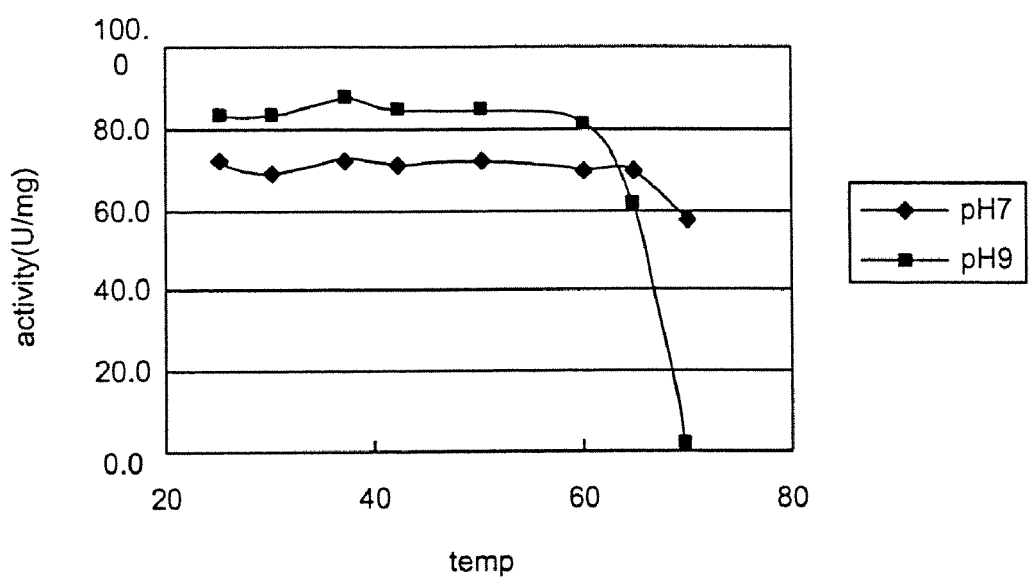
FIG. 6 shows the results of measuring the temperature stability of PtALD.

Residual activity was measured under the basic measurement conditions after incubating PtALD at 25 to 70° C. for 30 minutes in 100 mM potassium phosphate buffer (pH 7.0) and 100 mM glycine-NaOH buffer (pH 9.0). Those results are shown in FIG. 6.

Example 9

Synthesis of Substituted α-Keto Acid Using PtALD

The aldol condensation activity of the PtALD prepared in Example 4 was measured using acetaldehyde and α-ketobutyrate. A reaction solution composed of 100 mM glycine-NaOH (pH 9), 50 mM acetaldehyde, 250 mM α-ketobutyrate, 1 mM MgCl$_2$ and 0.1 mg/ml PtALD was prepared, and it was incubated at 33° C. for 16 hours. The resulting reaction solution was subjected to ultrafiltration with an ultrafiltration membrane, Microcon 10 (Amicon) for a fraction molecular weight of 10000. 10 μl of the filtrate was diluted in 200 μl of 50% acetonitrile/0.1% aqueous ammonia solution followed by ESI-MS analysis.

As a result, in contrast to the exact mass (calculated value) of the predicted product being 146.06, a peak (m/z=+146.8) of the m/z value corresponding to [M+H] was detected, thereby confirming formation of the desired aldol condensate according to the reaction shown below.

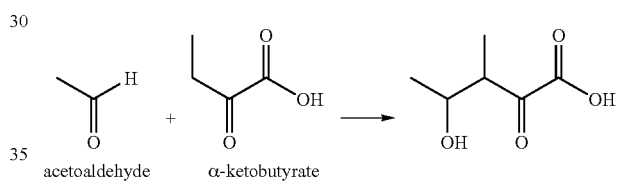

acetoaldehyde    α-ketobutyrate

Reference Example 1

Synthesis of 4-hydroxy-4-(3-Indolylmethyl)-2-ketoglutarate (IHOG)

7.50 g (35.8 mmol, content: 97.0% by weight) of indole-3-pyruvic acid and 14.18 g (107.4 mmol) of oxalacetic acid were added to 64.45 ml of aqueous solution including 18.91 g (286.5 mmol, content: 85% by weight) of potassium hydroxide and dissolved. This mixed solution was then stirred at 35° C. for 24 hours.

Furthermore, the mixed solution was neutralized (pH 7.0) by addition of 40.0 ml of 3 N hydrochloric acid to obtain 153.5 g of a neutralized reaction solution. This neutralized reaction solution contained 5.55 g of 4-hydroxy-4-(3-indolyl-methyl)-2-ketoglutarate, and the yield was 53.3% (with respect to indole pyruvic acid).

Water was added to this neutralized reaction solution to bring to a volume of 168 ml and then passed through a resin column (diameter: 4.8 cm) filled with 840 ml of a synthetic adsorbent (DIAION-SP207, Mitsubishi Chemical Corporation). Furthermore, water was passed through the column at a flow rate of 23.5 ml/min and by recovering the product from 1.73 to 2.55 (UL-R), an aqueous solution containing 3.04 g of highly pure 4-hydroxy-4-(3-indolylmethyl)-2-ketoglutarate was obtained at a yield of 54.7% (with respect to the amount charged into the resin).

(NMR Measurement)

$^1$H-NMR (400 MHz, D$_2$O): 3.03 (d, 1H, J=14.6 Hz), 3.11 (d, 1H, J=14.6 Hz), 3.21 (d, 1H, J=18.1 Hz), 3.40 (d, 1H, J=18.1 Hz), 7.06-7.15 (m, 3H), 7.39 (d, 1H, J=7.8 Hz), 7.66 (d, 1H, J=7.8 Hz)

$^{13}$C-NMR (100 MHz, D$_2$O): δ5.43, 47.91, 77.28, 109.49, 112.05, 119.44, 119.67, 121.91, 125.42, 128.41, 136.21, 169.78, 181.43, 203.58

Reference Example 2

Synthesis of 4-phenylmethyl-4-hydroxy-2-ketoglutarate (PHOG)

5.0 g (30.5 mmol) of phenylpyruvic acid and 12.1 g (91.4 mmol) of oxalacetic acid were added to 25 ml of water in which 13.8 g of potassium hydroxide (purity: 85%) was dissolved and the resulting mixture was allowed to react at room temperature for 72 hours. The pH value of this reaction solution was then adjusted to 2.2 using concentrated hydrochloric acid followed by extracting with ethyl acetate. After washing the organic layer with a saturated aqueous NaCl solution and drying with anhydrous magnesium sulfate and then concentrating, the residue was obtained. The residue was recrystallized from ethyl acetate and toluene to obtain 2.8 g (11.3 mmol) of 4-phenylmethyl-4-hydroxy-2-ketoglutarate in the form of crystals.

(NMR Measurement)

$^1$H-NMR (D$_2$O) δ: 2.48 (d, J=14.4 Hz, 0.18H), 2.60 (d, J=14.4 Hz, 0.18H), 2.85-3.30 (m, 3.64H), 7.17-7.36 (m, 5H)

(Measurement of Molecular Weight)

ESI-MS Calculated Value for $C_{12}H_{12}O_6$=252.23, analytical value=251.22 (MH$^-$)

Industrial Applicability

The aldolase of the present invention is a novel aldolase that catalyzes an aldol condensation reaction of indole pyruvic acid and pyruvic acid (or oxalacetic acid), and may be preferably used to synthesize 4-(indol-3-ylmethyl)-4-hydroxy-2-oxoglutarate (IHOG), which is useful as an intermediate in monatin synthesis.

We claim:
1. A process for producing a substituted α-keto acid of formula (3):

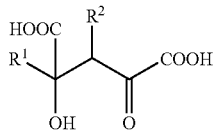

wherein
R¹ represents a hydrogen atom, an unsubstituted alkyl group having 1 to 8 carbon atoms, an alkyl group having 1 to 8 carbon atoms comprising at least one substituent, an unsubstituted alkoxyl group having 1 to 8 carbon atoms, an alkoxyl group having 1 to 8 carbon atoms comprising at least one substituent, an unsubstituted carboxyalkyl group having 2 to 9 carbon atoms, a carboxyalkyl group having 2 to 9 carbon atoms comprising at least one substituent, an unsubstituted aryl having up to 20 carbon atoms, an aryl having up to 20 carbon atoms comprising at least one substituent, an unsubstituted aralkyl group having up to 20 carbon atoms, an aralkyl group having up to 20 carbon atoms comprising at least one substituent, an unsubstituted heterocycle-containing hydrocarbon group having up to 11 carbon atoms, a heterocycle-containing hydrocarbon group having up to 11 carbon atoms comprising at least one substituent, a hydroxyl group or an ester derivative thereof,
wherein said substituent of R¹ is selected from the group consisting of a halogen atom, a hydroxyl group, an alkyl group having up to 3 carbon atoms, an alkoxy group having up to 3 carbon atoms, and an amino group; and
R² represents a hydrogen atom, an unsubstituted alkyl group having 1 to 8 carbon atoms, an alkyl group having 1 to 8 carbon atoms comprising at least one substituent, an unsubstituted alkoxyl group having 1 to 8 carbon atoms, an alkoxyl group having 1 to 8 carbon atoms comprising at least one substituent, an unsubstituted carboxyalkyl group having 2 to 9 carbon atoms, a carboxyalkyl group having 2 to 9 carbon atoms comprising at least one substituent, an unsubstituted aryl having up to 20 carbon atoms, an aryl having up to 20 carbon atoms comprising at least one substituent, an unsubstituted aralkyl group having up to 20 carbon atoms, an aralkyl group having up to 20 carbon atoms comprising at least one substituent, an unsubstituted heterocycle-containing hydrocarbon group having up to 11 carbon atoms, a heterocycle-containing hydrocarbon group having up to 11 carbon atoms comprising at least one substituent, a hydroxyl group or an ester derivative thereof, wherein said substituent of $R^2$ is selected from the group consisting of a halogen atom, a hydroxyl group, an alkyl group having up to 3 carbon atoms, an alkoxy group having up to 3 carbon atoms and an amino group; and when $R^1$ represents a hydrogen atom, a methyl group or a carboxymethyl group in formula (1), $R^2$ does not represent a hydrogen atom;

comprising a reaction of the substituted α-keto acid of formula (1):

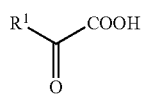

(1)

wherein $R^1$ has the same meaning as $R^1$ in formula (3), with the substituted α-keto acid of formula (2):

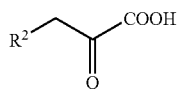

(2)

wherein $R^2$ has the same meaning as $R^2$ in formula (3);

wherein the reaction is catalyzed by a protein that has aldolase activity and is selected from the group consisting of:

a protein comprising the amino acid sequence of SEQ ID NO: 2;

a protein comprising the amino acid sequence of residue numbers 5 to 225 of SEQ ID NO: 2;

a protein having the amino acid sequence of SEQ ID NO: 2 except that it contains substitution, deletion, insertion, or addition of one to ten amino acid residues in the amino acid sequence of SEQ ID NO: 2; and a protein having the amino acid sequence of residue numbers 5 to 225 of SEQ ID NO: 2 except that it contains substitution, deletion, insertion, or addition of one to ten amino acid residues in the acid sequence of residue numbers 5 to 225 of SEQ ID NO: 2.

2. The process according to claim 1, wherein $R^2$ is a hydrogen atom or a carboxyl group.

3. The process according to claim 2, wherein $R^2$ is a hydrogen atom.

4. The process according to claim 1, wherein $R^1$ is a benzyl group or a 3-indolylmethyl group, and $R^2$ is a hydrogen atom or a carboxyl group.

5. A process for producing a substituted α-keto acid of formula (3'):

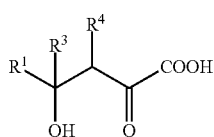

(3')

wherein $R^1$ represents a hydrogen atom, an unsubstituted alkyl group having 1 to 8 carbon atoms, an alkyl group having 1 to 8 carbon atoms comprising at least one substituent, an unsubstituted alkoxyl group having 1 to 8 carbon atoms, an alkoxyl group having 1 to 8 carbon atoms comprising at least one substituent, an unsubstituted carboxyalkyl group having 2 to 9 carbon atoms, a carboxyalkyl group having 2 to 9 carbon atoms comprising at least one substituent, an unsubstituted aryl having up to 20 carbon atoms, an aryl having up to 20 carbon atoms comprising at least one substituent, an unsubstituted aralkyl group having up to 20 carbon atoms, an aralkyl group having up to 20 carbon atoms comprising at least one substituent, an unsubstituted heterocycle-containing hydrocarbon group having up to 11 carbon atoms, a heterocycle-containing hydrocarbon group having up to 11 carbon atoms comprising at least one substituent, a hydroxyl group or an ester derivative thereof, wherein said substituent of $R^1$ is selected from the group consisting of a halogen atom, a hydroxyl group, an alkyl group having up to 3 carbon atoms, an alkoxy group having up to 3 carbon atoms, and an amino group $R^3$ represents a hydrogen atom or a carboxyl group; and $R^4$ represents a hydrogen atom, an unsubstituted alkyl group having 1 to 8 carbon atoms, an alkyl group having 1 to 8 carbon atoms comprising at least one substituent, an unsubstituted alkoxyl group having 1 to 8 carbon atoms, an alkoxyl group having 1 to 8 carbon atoms comprising at least one substituent, an unsubstituted carboxyalkyl group having 2 to 9 carbon atoms, a carboxyalkyl group having 2 to 9 carbon atoms comprising at least one substituent, an unsubstituted aryl having up to 20 carbon atoms, an aryl having up to 20 carbon atoms comprising at least one substituent, an unsubstituted aralkyl group having up to 20 carbon atoms, an aralkyl group having up to 20 carbon atoms comprising at least one substituent, an unsubstituted heterocycle-containing hydrocarbon group having up to 11 carbon atoms, a heterocycle-containing hydrocarbon group having up to 11 carbon atoms comprising at least one substituent, a hydroxyl group or an ester derivative thereof, wherein said substituent of $R^4$ is selected from the group consisting of a halogen atom, a hydroxyl group, an alkyl group having up to 3 carbon atoms, an alkoxy group having up to 3 carbon atoms, and an amino group;

comprising a reaction of the compound of formula (1'):

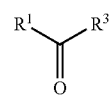

(1')

wherein $R^1$ and $R^3$ have the same meanings as defined in formula (3'), with the substituted α-keto acid of formula (2'):

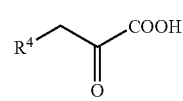

(2')

wherein $R^4$ has the same meaning as defined in formula (3');

wherein the protein that catalyzes the reaction is a protein that has aldolase activity and is selected from the group consisting of:

a protein comprising the amino acid sequence of SEQ ID NO: 2;

a protein comprising the amino acid sequence of residue numbers 5 to 225 of SEQ ID NO: 2;

a protein having the amino acid sequence of SEQ ID NO: 2 except that it contains substitution, deletion, insertion, or addition of one to ten amino acid residues in the amino acid sequence of SEQ ID NO: 2; and a protein having the amino acid sequence of residue numbers 5 to 225 of SEQ ID NO: 2 except that it contains substitution, deletion, insertion, or addition of one to ten amino acid residues in the acid sequence of residue numbers 5 to 225 of SEQ ID NO: 2.

6. The process according to claim 5, wherein $R^4$ is a hydrogen atom or a carboxyl group.

7. A process for producing a substituted α-keto acid of formula (4):

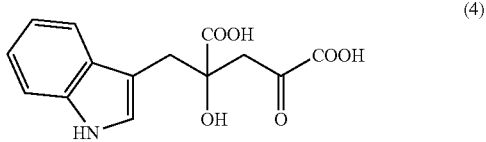

(4)

from oxaloacetic acid or pyruvic acid, and indole-3-pyruvic acid wherein the reaction is catalyzed by a protein that has aldolase activity and is selected from the group consisting of:

a protein comprising the amino acid sequence of SEQ ID NO: 2;

a protein comprising the amino acid sequence of residue numbers 5 to 225 of SEQ ID NO: 2;

a protein having the amino acid sequence of SEQ ID NO: 2 except that it contains substitution, deletion, insertion, or addition of one to ten amino acid residues in the amino acid sequence of SEQ ID NO: 2; and a protein having the amino acid sequence of residue numbers 5 to 225 of SEQ ID NO: 2 except that it contains substitution, deletion, insertion, or addition of one to ten amino acid residues in the acid sequence of residue numbers 5 to 225 of SEQ ID NO: 2.

8. The process according to claim 1, wherein said protein is a protein that comprises the amino acid sequence of SEQ ID NO: 2.

9. The process according to claim 1, wherein said protein is a protein that comprises the amino acid sequence of residue numbers 5 to 225 of SEQ ID NO: 2.

10. The process according to claim 1, wherein said protein is a protein that has the amino acid sequence of SEQ ID NO: 2 except that it contains substitution, deletion, insertion, or addition of one to ten amino acid residues in the amino acid sequence of SEQ ID NO: 2.

11. The process according to claim 5, wherein said protein is a protein that comprises the amino acid sequence of SEQ ID NO: 2.

12. The process according to claim 5, wherein said protein is a protein that comprises the amino acid sequence of residue numbers 5 to 225 of SEQ ID NO: 2.

13. The process according to claim 5, wherein said protein is a protein that has the amino acid sequence of SEQ ID NO: 2 except that it contains substitution, deletion, insertion, or addition of one to ten amino acid residues in the amino acid sequence of SEQ ID NO: 2.

14. The process according to claim 7, wherein said protein is a protein that comprises the amino acid sequence of SEQ ID NO: 2.

15. The process according to claim 7, wherein said protein is a protein that comprises the amino acid sequence of residue numbers 5 to 225 of SEQ ID NO: 2.

16. The process according to claim 7, wherein said protein is a protein that has the amino acid sequence of SEQ ID NO: 2 except that it contains substitution, deletion, insertion, or addition of one to ten amino acid residues in the amino acid sequence of SEQ ID NO: 2.

17. The process according to claim 1, wherein said protein is a protein that has the amino acid sequence of residue numbers 5 to 225 of SEQ ID NO: 2 except that it contains substitution, deletion, insertion, or addition of one to ten amino acid residues in the acid sequence of residue numbers 5 to 225 of SEQ ID NO: 2.

18. The process according to claim 5, wherein said protein is a protein that has the amino acid sequence of residue numbers 5 to 225 of SEQ ID NO: 2 except that it contains substitution, deletion, insertion, or addition of one to ten amino acid residues in the acid sequence of residue numbers 5 to 225 of SEQ ID NO: 2.

19. The process according to claim 7, wherein said protein is a protein that has the amino acid sequence of residue numbers 5 to 225 of SEQ ID NO: 2 except that it contains substitution, deletion, insertion, or addition of one to ten amino acid residues in the acid sequence of residue numbers 5 to 225 of SEQ ID NO: 2.

* * * * *

SEQUENCE LISTING

```
<160> NUMBER OF SEQ ID NOS: 16

<210> SEQ ID NO 1
<211> LENGTH: 1296
<212> TYPE: DNA
<213> ORGANISM: Pseudomonas taetrolens
<220> FEATURE:
<221> NAME/KEY: CDS
<222> LOCATION: (444)..(1118)
<220> FEATURE:
<221> NAME/KEY: misc_feature
<222> LOCATION: (456)..(1118)
<223> OTHER INFORMATION: Alternate coding frame, see SEQ ID NO: 3

<400> SEQUENCE: 1
gtacaccgtc ctgactcagg gcgcgctcgg cacgggttga tctatgagcg ctgtttgccc      60
agaatgacgt cggggtcacg tacgatcaaa gcaactacct gatcgcccag tgggcctgac     120
ctgtccggtg tcggcatcag ctacctgcct cgccaagtgt ctctcgccat ggtggacca      180 gggtcgggct actagtcatc gaaaccgagc ctgcgctgcc tcccatccaa tacatcgccg     240
tacaccgcgc cgatcgtctt cagggcctca gcgtcgaggt tgcacgtctg gcagctcgtt     300
gctgtgattt cagccgcatg gtgtggtaac acaggcgctg gatacgagaa aaaaagcgat     360
gtattttcat agataaatat cgctaatagt gccaagcgac ctttcttact atgaacgcat     420
agcccacaag ggttcagtca ttc atg gag gtc gct atg tca ttg ccc ggt tca      473
                       Met Glu Val Ala Met Ser Leu Pro Gly Ser
                         1               5                  10 cgc atc tac cct tct ccg ccc cag gca cca cgc tca ctg ctg gac gcg      521
Arg Ile Tyr Pro Ser Pro Pro Gln Ala Pro Arg Ser Leu Leu Asp Ala
            15                  20                  25 ttt cag aac gta gtg acg ccg cat atc agt gat aac ctc ggg cgt cac      569
Phe Gln Asn Val Val Thr Pro His Ile Ser Asp Asn Leu Gly Arg His
        30                  35                  40 atc ggt gcc cgg ggg ctg acg cgc tat aac cac acc ggc aaa ctg gtg      617
Ile Gly Ala Arg Gly Leu Thr Arg Tyr Asn His Thr Gly Lys Leu Val
    45                  50                  55 ggc acc gcc ctg acg gtg aag act cgc ccc ggc gac aac ctc tac atc      665
Gly Thr Ala Leu Thr Val Lys Thr Arg Pro Gly Asp Asn Leu Tyr Ile
```

```
             60                  65                    70
tac aaa gca ctg acg ctg atc gaa ccc gga cac gtg ctg gtg atc gac      713
Tyr Lys Ala Leu Thr Leu Ile Glu Pro Gly His Val Leu Val Ile Asp
 75                  80                    85                  90 gct cag ggt gac gcg acc aac gcg gtc att ggt gag ctg atc aag ctc      761
Ala Gln Gly Asp Ala Thr Asn Ala Val Ile Gly Glu Leu Ile Lys Leu
                 95                    100                 105 tac gcg cag caa cgt ggc tgt gtc ggc ttc gtc gtc gac ggc gcc atc      809
Tyr Ala Gln Gln Arg Gly Cys Val Gly Phe Val Val Asp Gly Ala Ile
                     110                   115                 120 cgc gat gtc gcc agt ttt gaa gat acg cct tgc tat gcc cgt agc gtg      857
Arg Asp Val Ala Ser Phe Glu Asp Thr Pro Cys Tyr Ala Arg Ser Val
                125                   130                 135 gtg cat tgc ggt ccc tac aaa agc ggc cca ggg gaa atc aat gtc ccg      905
Val His Cys Gly Pro Tyr Lys Ser Gly Pro Gly Glu Ile Asn Val Pro
    140                   145                   150 gtg tca atc ggc ggg atg atc atc aat ccg ggc gac atc att gtc ggt      953
Val Ser Ile Gly Gly Met Ile Ile Asn Pro Gly Asp Ile Ile Val Gly
155                   160                   165                 170 gac gag gat ggg ctg gtt gcc ttc tcg ccc gac cat gcc gag cag gtg      1001
Asp Glu Asp Gly Leu Val Ala Phe Ser Pro Asp His Ala Glu Gln Val
                    175                   180                 185 ttg gtc aag gcg cga gag cat gac gcg cat gaa cag cag gtc aaa gcc      1049
Leu Val Lys Ala Arg Glu His Asp Ala His Glu Gln Gln Val Lys Ala
                190                   195                 200 gaa atc gcc act ggc gcc atc gat cag tca tgg ctg gac aaa gtg ctg      1097
Glu Ile Ala Thr Gly Ala Ile Asp Gln Ser Trp Leu Asp Lys Val Leu
            205                   210                 215 gaa aag gct ggc ctg gcg aac tgaaaaacac tgtgtaatcg ccttgctgca         1148
Glu Lys Ala Gly Leu Ala Asn
        220                   225 gcgacattgc tgtcggacag gatgatctga cgcttcagtt acgcgttctt gggtgcaccg    1208
cgccacgtca ggaagtggct gctgccgcat gcaggtgaca tgtcatgtac catggcagca    1268
gcacgtgaca tgcacgatgt gctcacgc                                       1296

<210> SEQ ID NO 2
<211> LENGTH: 225
<212> TYPE: PRT
<213> ORGANISM: Pseudomonas taetrolens

<400> SEQUENCE: 2

Met Glu Val Ala Met Ser Leu Pro Gly Ser Arg Ile Tyr Pro Ser Pro
1               5                   10                  15

Pro Gln Ala Pro Arg Ser Leu Leu Asp Ala Phe Gln Asn Val Val Thr
            20                  25                  30

Pro His Ile Ser Asp Asn Leu Gly Arg His Ile Gly Ala Arg Gly Leu
        35                  40                  45

Thr Arg Tyr Asn His Thr Gly Lys Leu Val Gly Thr Ala Leu Thr Val
    50                  55                  60

Lys Thr Arg Pro Gly Asp Asn Leu Tyr Ile Tyr Lys Ala Leu Thr Leu
65                  70                  75                  80

Ile Glu Pro Gly His Val Leu Val Ile Asp Ala Gln Gly Asp Ala Thr
                85                  90                  95

Asn Ala Val Ile Gly Glu Leu Ile Lys Leu Tyr Ala Gln Gln Arg Gly
            100                 105                 110

Cys Val Gly Phe Val Val Asp Gly Ala Ile Arg Asp Val Ala Ser Phe
        115                 120                 125
```

-continued

```
Glu Asp Thr Pro Cys Tyr Ala Arg Ser Val Val His Cys Gly Pro Tyr
            130                 135                 140

Lys Ser Gly Pro Gly Glu Ile Asn Val Pro Val Ser Ile Gly Gly Met
145                 150                 155                 160

Ile Ile Asn Pro Gly Asp Ile Val Gly Asp Glu Asp Gly Leu Val
                165                 170                 175

Ala Phe Ser Pro Asp His Ala Glu Gln Val Leu Val Lys Ala Arg Glu
                180                 185                 190

His Asp Ala His Glu Gln Gln Val Lys Ala Glu Ile Ala Thr Gly Ala
                195                 200                 205

Ile Asp Gln Ser Trp Leu Asp Lys Val Leu Glu Lys Ala Gly Leu Ala
    210                 215                 220

Asn
225

<210> SEQ ID NO 3
<211> LENGTH: 221
<212> TYPE: PRT
<213> ORGANISM: Pseudomonas taetrolens

<400> SEQUENCE: 3

Met Ser Leu Pro Gly Ser Arg Ile Tyr Pro Ser Pro Gln Ala Pro
1               5                   10                  15

Arg Ser Leu Leu Asp Ala Phe Gln Asn Val Val Thr Pro His Ile Ser
                20                  25                  30

Asp Asn Leu Gly Arg His Ile Gly Ala Arg Gly Leu Thr Arg Tyr Asn
            35                  40                  45

His Thr Gly Lys Leu Val Gly Thr Ala Leu Thr Val Lys Thr Arg Pro
    50                  55                  60

Gly Asp Asn Leu Tyr Ile Tyr Lys Ala Leu Thr Leu Ile Glu Pro Gly
65                  70                  75                  80

His Val Leu Val Ile Asp Ala Gln Gly Asp Ala Thr Asn Ala Val Ile
                85                  90                  95

Gly Glu Leu Ile Lys Leu Tyr Ala Gln Gln Arg Gly Cys Val Gly Phe
                100                 105                 110

Val Val Asp Gly Ala Ile Arg Asp Val Ala Ser Phe Glu Asp Thr Pro
            115                 120                 125

Cys Tyr Ala Arg Ser Val Val His Cys Gly Pro Tyr Lys Ser Gly Pro
    130                 135                 140

Gly Glu Ile Asn Val Pro Val Ser Ile Gly Gly Met Ile Ile Asn Pro
145                 150                 155                 160

Gly Asp Ile Ile Val Gly Asp Glu Asp Gly Leu Val Ala Phe Ser Pro
                165                 170                 175

Asp His Ala Glu Gln Val Leu Val Lys Ala Arg Glu His Asp Ala His
                180                 185                 190

Glu Gln Gln Val Lys Ala Glu Ile Ala Thr Gly Ala Ile Asp Gln Ser
            195                 200                 205

Trp Leu Asp Lys Val Leu Glu Lys Ala Gly Leu Ala Asn
    210                 215                 220

<210> SEQ ID NO 4
<211> LENGTH: 20
<212> TYPE: PRT
<213> ORGANISM: Pseudomonas taetrolens

<400> SEQUENCE: 4

Ser Leu Leu Asp Ala Phe Gln Asn Val Val Thr Pro His Ile Ser Asp
```

-continued

```
                1               5                  10                 15

Asn Leu Gly Arg
            20

<210> SEQ ID NO 5
<211> LENGTH: 12
<212> TYPE: PRT
<213> ORGANISM: Pseudomonas taetrolens

<400> SEQUENCE: 5

Ala Glu Ile Ala Thr Gly Ala Leu Asp Gln Ser Trp
1               5                   10

<210> SEQ ID NO 6
<211> LENGTH: 22
<212> TYPE: DNA
<213> ORGANISM: Artificial Sequence
<220> FEATURE:
<223> OTHER INFORMATION: Synthetic DNA

<400> SEQUENCE: 6
ttycaraayg tsgtsacscc sc                                                  22

<210> SEQ ID NO 7
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 7
tgrtcratng cnccsgtngc ratytcngc                                           29

<210> SEQ ID NO 8
<211> LENGTH: 31
<212> TYPE: DNA
<213> ORGANISM: Artificial Sequence
<220> FEATURE:
<223> OTHER INFORMATION: Synthetic DNA

<400> SEQUENCE: 8
gccggatcca caagggttca gtcattcatg g                                        31

<210> SEQ ID NO 9
<211> LENGTH: 28
<212> TYPE: DNA
<213> ORGANISM: Artificial Sequence
<220> FEATURE:
<223> OTHER INFORMATION: Synthetic DNA

<400> SEQUENCE: 9
ccgaagcttt cagttcgcca ggccagcc                                            28
```

```
<210> SEQ ID NO 10
<211> LENGTH: 40
<212> TYPE: DNA
<213> ORGANISM: Artificial Sequence
<220> FEATURE:
<223> OTHER INFORMATION: Synthetic DNA

<400> SEQUENCE: 10
gtatcacgag gccctagctg tggtgtcatg gtcggtgatc                             40

<210> SEQ ID NO 11
<211> LENGTH: 40
<212> TYPE: DNA
<213> ORGANISM: Artificial Sequence
<220> FEATURE:
<223> OTHER INFORMATION: Synthetic DNA

<400> SEQUENCE: 11
ttcggggatt ccatatgata ccctttttac gtgaacttgc                             40

<210> SEQ ID NO 12
<211> LENGTH: 38
<212> TYPE: DNA
<213> ORGANISM: Artificial Sequence
<220> FEATURE:
<223> OTHER INFORMATION: Synthetic DNA

<400> SEQUENCE: 12
ggggggggca tatgcgacct ccttattacg tgaacttg                               38

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
ggttcagtca catatggagg tcgctatgtc                                        30

<210> SEQ ID NO 14
<211> LENGTH: 33
<212> TYPE: DNA
<213> ORGANISM: Artificial Sequence
<220> FEATURE:
<223> OTHER INFORMATION: Synthetic DNA

<400> SEQUENCE: 14
atggaggtcc attagtcatt gcccggttca cgc                                    33

<210> SEQ ID NO 15
<211> LENGTH: 1176
<212> TYPE: DNA
<213> ORGANISM: Pseudomonas coronafaciens
<220> FEATURE:
<221> NAME/KEY: CDS
<222> LOCATION: (398)..(1141)

<400> SEQUENCE: 15
gtcgtaaccc acaccgtgct tggcaatgat cttcagattg cctgaggcct ggatcatgtc       60
cttggtcagc ttgccttggc gcacgatgat cgcgtgaggt tgttcgtcgc ggattattgc      120
agtcagctct cggcgggca tgtagggcgt ggtggggatg atggtaatgc cttgagatgc       180
ggcgtaggcc atcgcatcgg ctgccagttc ggggcctgtc agcaggatct tccgattcat      240
gatcgatacc ttgtttttat agaggtcgtg tgcggcgtcg agaagacatc tgcacctggc      300
```

```
tgaaccctac cataatgaaa tgtcgttgca atatagatga attgataatc ttgatgagtg     360 gttttatt gggtatccgc ctattgatcc tgttaaa atg aaa tgt cat tct gtt      415
                                        Met Lys Cys His Ser Val
                                        1               5 att tgg ttt agt gcc tgg ccg cat cca ata att tca aga gag aaa agc      463
Ile Trp Phe Ser Ala Trp Pro His Pro Ile Ile Ser Arg Glu Lys Ser
         10                  15                  20 cac atg acg atc gga ttc aga gtt ctc agt gca gcc cgc aaa gtc agc      511
His Met Thr Ile Gly Phe Arg Val Leu Ser Ala Ala Arg Lys Val Ser
             25                  30                  35 ccg gaa tgg gtc gcc cgc tac cgc gat gtt ccg gtg gcc aat gtc agt      559
Pro Glu Trp Val Ala Arg Tyr Arg Asp Val Pro Val Ala Asn Val Ser
    40                  45                  50 gac tcg atg aac cgg atg acc gct ggg ggg tcc agg ctg cgc ccc atg      607
Asp Ser Met Asn Arg Met Thr Ala Gly Gly Ser Arg Leu Arg Pro Met
55                  60                  65                  70 cac cgt gcg ggc gtt ctc gcc ggg ccg gcc ttg acg gtc aag gcc cgt      655
His Arg Ala Gly Val Leu Ala Gly Pro Ala Leu Thr Val Lys Ala Arg
                 75                  80                  85 ccg ggt gac aac ctg atg ctg cat tac gct att gat att gct cag ccg      703
Pro Gly Asp Asn Leu Met Leu His Tyr Ala Ile Asp Ile Ala Gln Pro
         90                  95                  100 ggc gac gtg att gtg gtg gat gcc ggg ggc gac ctg act aac gcg ctg      751
Gly Asp Val Ile Val Val Asp Ala Gly Gly Asp Leu Thr Asn Ala Leu
             105                 110                 115 att ggc gaa atg atg gtg gct tat gct gta aaa cgt ggt gtg gct ggc      799
Ile Gly Glu Met Met Val Ala Tyr Ala Val Lys Arg Gly Val Ala Gly
    120                 125                 130 atc gtc atc aac ggc gcc atc cgt gat gcc gcc agc atc ggt gca ggc      847
Ile Val Ile Asn Gly Ala Ile Arg Asp Ala Ala Ser Ile Gly Ala Gly
135                 140                 145                 150 gac ttc ccg atg ttt gca gcc ggt gta tcg cat cgg ggt cct tat aaa      895
Asp Phe Pro Met Phe Ala Ala Gly Val Ser His Arg Gly Pro Tyr Lys
                 155                 160                 165 gac ggg cca ggc gaa atc aat gtc ccg atc gcc atc gac ggc atg gtc      943
Asp Gly Pro Gly Glu Ile Asn Val Pro Ile Ala Ile Asp Gly Met Val
         170                 175                 180 atc gag gcg ggg gat ctg gtg ata ggc gat gac gac ggc ttg ctg tgt      991
Ile Glu Ala Gly Asp Leu Val Ile Gly Asp Asp Asp Gly Leu Leu Cys
             185                 190                 195 gtc cct tac gac cag gtt gca gag gtg tat gac cgg gca gca gcc aag      1039
Val Pro Tyr Asp Gln Val Ala Glu Val Tyr Asp Arg Ala Ala Ala Lys
    200                 205                 210 cat cat gca gag caa aag caa ctg gag cag atc gcc aag ggc gaa aat      1087
His His Ala Glu Gln Lys Gln Leu Glu Gln Ile Ala Lys Gly Glu Asn
215                 220                 225                 230 gat cgc tcc tgg gta ctt gaa tca ttg aag aaa aaa ggc tgc cag ctt      1135
Asp Arg Ser Trp Val Leu Glu Ser Leu Lys Lys Lys Gly Cys Gln Leu
                 235                 240                 245 cca gaa tgagctggtg taatcgtgcc tttcgcgcac gatct                       1176
Pro Glu <210> SEQ ID NO 16
<211> LENGTH: 248
<212> TYPE: PRT
<213> ORGANISM: Pseudomonas coronafaciens

<400> SEQUENCE: 16

Met Lys Cys His Ser Val Ile Trp Phe Ser Ala Trp Pro His Pro Ile
1               5                   10                  15
```

```
Ile Ser Arg Glu Lys Ser His Met Thr Ile Gly Phe Arg Val Leu Ser
        20              25              30

Ala Ala Arg Lys Val Ser Pro Glu Trp Val Ala Arg Tyr Arg Asp Val
        35              40              45

Pro Val Ala Asn Val Ser Asp Ser Met Asn Arg Met Thr Ala Gly Gly
    50              55              60

Ser Arg Leu Arg Pro Met His Arg Ala Gly Val Leu Ala Gly Pro Ala
65          70              75              80

Leu Thr Val Lys Ala Arg Pro Gly Asp Asn Leu Met Leu His Tyr Ala
            85              90              95

Ile Asp Ile Ala Gln Pro Gly Asp Val Ile Val Val Asp Ala Gly Gly
            100             105             110

Asp Leu Thr Asn Ala Leu Ile Gly Glu Met Met Val Ala Tyr Ala Val
        115             120             125

Lys Arg Gly Val Ala Gly Ile Val Ile Asn Gly Ala Ile Arg Asp Ala
        130             135             140

Ala Ser Ile Gly Ala Gly Asp Phe Pro Met Phe Ala Ala Gly Val Ser
145             150             155             160

His Arg Gly Pro Tyr Lys Asp Gly Pro Gly Glu Ile Asn Val Pro Ile
                165             170             175

Ala Ile Asp Gly Met Val Ile Glu Ala Gly Asp Leu Val Ile Gly Asp
            180             185             190

Asp Asp Gly Leu Leu Cys Val Pro Tyr Asp Gln Val Ala Glu Val Tyr
        195             200             205

Asp Arg Ala Ala Ala Lys His His Ala Glu Gln Lys Gln Leu Glu Gln
        210             215             220

Ile Ala Lys Gly Glu Asn Asp Arg Ser Trp Val Leu Glu Ser Leu Lys
225             230             235             240

Lys Lys Gly Cys Gln Leu Pro Glu
                245
```